(12) United States Patent
Godron et al.

(10) Patent No.: US 12,428,668 B2
(45) Date of Patent: Sep. 30, 2025

(54) ONE POT SYNTHESIS OF SETS OF OLIGONUCLEOTIDES

(71) Applicant: DNA Script, Le Kremlin-Bicêtre (FR)

(72) Inventors: Xavier Godron, Le Kremlin-Bicêtre (FR); Adrian Horgan, Le Kremlin-Bicêtre (FR)

(73) Assignee: DNA Script, Le Kremlin-Bicêtre (FR)

( * ) Notice: Subject to any disclaimer, the term of this patent is extended or adjusted under 35 U.S.C. 154(b) by 941 days.

(21) Appl. No.: 17/419,637

(22) PCT Filed: Dec. 26, 2019

(86) PCT No.: PCT/EP2019/087048
§ 371 (c)(1),
(2) Date: Jun. 29, 2021

(87) PCT Pub. No.: WO2020/141143
PCT Pub. Date: Jul. 9, 2020

(65) Prior Publication Data
US 2022/0356510 A1     Nov. 10, 2022

(30) Foreign Application Priority Data

Jan. 3, 2019 (EP) .................................. 19305007

(51) Int. Cl.
| C12Q 1/6806 | (2018.01) |
| C12Q 1/48 | (2006.01) |
| C12Q 1/686 | (2018.01) |

(52) U.S. Cl.
CPC ............. *C12Q 1/6806* (2013.01); *C12Q 1/48* (2013.01); *C12Q 1/686* (2013.01)

(58) Field of Classification Search
CPC ......... C12Q 1/6806; C12Q 1/686; C12Q 1/48
See application file for complete search history.

(56) References Cited

U.S. PATENT DOCUMENTS

| 4,683,195 A | 7/1987 | Mullis et al. |
| 4,683,202 A | 7/1987 | Mullis |
| (Continued) | | |

FOREIGN PATENT DOCUMENTS

| CN | 101835903 A | 9/2010 |
| EP | 0303459 A2 | 2/1989 |
| (Continued) | | |

OTHER PUBLICATIONS

Becker, et al., (1967) "The Enzymatic Cleavage of Phosphate Termini from Polynucleotides", The Journal Biological Chemistry, vol. 242, No. 5, pp. 936-950.

(Continued)

*Primary Examiner* — Gary Benzion
*Assistant Examiner* — Lisa Horth
(74) *Attorney, Agent, or Firm* — MORRISON & FOERSTER LLP

(57) ABSTRACT

The invention is directed to methods for synthesizing a plurality of oligonucleotides in the same reaction vessel, and in some embodiments, using the synthesized oligonucleotides in an oligonucleotide-based assay in such reaction vessel. In some embodiments, methods of the invention are implemented by steps of (a) providing a plurality of different initiators attached to one or more supports, each different initiator having a terminal nucleotide with a different 3-O-blocking group; (b) for each different initiator, synthesizing a polynucleotide by repeated cycles of template-free enzymatic additions of 3'-O-blocked nucleoside triphosphates, wherein the blocking group of the 3-O-blocked nucleoside triphosphate is removable under deblocking conditions orthogonal to the deblocking conditions for removing blocking groups of the other initiators; and (c) releasing the oligonucleotides from the polynucleotides and the one or more solid supports.

18 Claims, 11 Drawing Sheets

Specification includes a Sequence Listing.

(56) References Cited

U.S. PATENT DOCUMENTS

| | | | |
|---|---|---|---|
| 4,800,159 | A | 1/1989 | Mullis et al. |
| 4,965,188 | A | 10/1990 | Mullis et al. |
| 5,126,022 | A | 6/1992 | Soane et al. |
| 5,168,038 | A | 12/1992 | Tecott et al. |
| 5,210,015 | A | 5/1993 | Gelfand et al. |
| 5,367,066 | A | 11/1994 | Urdea et al. |
| 5,399,491 | A | 3/1995 | Kacian et al. |
| 5,436,143 | A | 7/1995 | Hyman |
| 5,498,392 | A | 3/1996 | Wilding et al. |
| 5,587,128 | A | 12/1996 | Wilding et al. |
| 5,635,400 | A | 6/1997 | Brenner |
| 5,700,642 | A | 12/1997 | Monforte et al. |
| 5,739,386 | A | 4/1998 | Holmes |
| 5,763,594 | A | 6/1998 | Hiatt et al. |
| 5,808,045 | A | 9/1998 | Hiatt et al. |
| 5,830,655 | A | 11/1998 | Monforte et al. |
| 5,854,033 | A | 12/1998 | Lizardi |
| 5,858,195 | A | 1/1999 | Ramsey |
| 5,925,517 | A | 7/1999 | Tyagi et al. |
| 5,981,179 | A | 11/1999 | Lorinez et al. |
| 6,001,229 | A | 12/1999 | Ramsey |
| 6,010,607 | A | 1/2000 | Ramsey |
| 6,033,546 | A | 3/2000 | Ramsey |
| 6,054,034 | A | 4/2000 | Soane et al. |
| 6,174,670 | B1 | 1/2001 | Wittwer et al. |
| 6,399,952 | B1 | 6/2002 | Maher et al. |
| 6,569,627 | B2 | 5/2003 | Wittwer et al. |
| 6,613,525 | B2 | 9/2003 | Nelson et al. |
| 6,960,437 | B2 | 11/2005 | Enzelberger et al. |
| 7,057,026 | B2 | 6/2006 | Barnes et al. |
| 7,537,897 | B2 | 5/2009 | Brenner et al. |
| 7,544,794 | B1 | 6/2009 | Benner |
| 7,795,454 | B2 | 9/2010 | Jiang et al. |
| 8,034,923 | B1 | 10/2011 | Benner et al. |
| 8,212,020 | B2 | 7/2012 | Benner et al. |
| 8,808,988 | B2 | 8/2014 | Zhao et al. |
| 8,808,989 | B1 | 8/2014 | Efcavitch et al. |
| 10,435,676 | B2 | 10/2019 | Champion et al. |
| 2003/0186226 | A1 | 10/2003 | Brennan et al. |
| 2004/0106728 | A1 | 6/2004 | McGall et al. |
| 2005/0037991 | A1 | 2/2005 | Bodepudi et al. |
| 2011/0097716 | A1 | 4/2011 | Natt et al. |
| 2011/0104785 | A1 | 5/2011 | Vaidyanathan et al. |
| 2011/0143964 | A1* | 6/2011 | Zhou ............... C07H 21/04 506/40 |
| 2016/0108382 | A1 | 4/2016 | Efcavitch et al. |
| 2018/0201968 | A1 | 7/2018 | Chen et al. |
| 2019/0078065 | A1 | 3/2019 | Baiga et al. |
| 2019/0078126 | A1 | 3/2019 | Baiga et al. |

FOREIGN PATENT DOCUMENTS

| | | |
|---|---|---|
| EP | 0799897 A1 | 10/1997 |
| JP | 4-262799 | 9/1992 |
| JP | 3974441 B2 | 9/2007 |
| WO | WO1991006678 | 5/1991 |
| WO | WO1999019717 | 4/1999 |
| WO | WO2002024322 | 3/2002 |
| WO | WO2004005667 | 1/2004 |
| WO | WO2015159023 | 10/2015 |
| WO | 2016/128731 A1 | 8/2016 |
| WO | WO2017009663 | 1/2017 |
| WO | WO2017156218 | 9/2017 |
| WO | WO2017216472 | 12/2017 |
| WO | 2018/152323 A1 | 8/2018 |
| WO | WO2019135007 | 7/2019 |
| WO | 2020/165137 A1 | 8/2020 |
| WO | 2021/058438 A1 | 4/2021 |

OTHER PUBLICATIONS

Becker-Andre, et al., (1989) "Absolute mRNA quantification using the polymerase chain reaction (PCR), A novel approach by a PCR aided transcript titration assay (PATTY)", Nucleic Acids Research, vol. 17, No. 22, pp. 9437-9446.

Bernard, et al., (1999) "Color Multiplexing Hybridization Probes Using the Apolipoprotein E. Locus as a Model System for Genotyping", Analytical Biochemistry, vol. 273, pp. 221-228.

Brenner, et al., (2000) "In vitro cloning of complex mixtures of DNA on microbeads: Physical separation of differentially expressed cDNAs", Proceedings of the National Academy of Sciences, vol. 97, No. 4, pp. 1665-1670.

Cameron, et al., (1977) "3'-Phosphatase Activity in T4 Polynucleotide Kinase", Biochemistry, vol. 16, No. 23, pp. 5120-5126.

Canard, et al., (1994) "DNA polymerase fluorescent substrates with reversible 3'-tags", Gene, vol. 148, pp. 1-6.

Canard, et al., (1995) "Catalytic editing properties of DNA polymerases", Proceedings of the National Academy of Sciences, vol. 92, pp. 10859-10863.

Deiman et al, (2002) "Characteristics and Applications of Nucleic Acid Sequence-Based Amplification (NASBA)", Molecular Biotechnology, vol. 20, pp. 163-179.

Delarue, et al., (2002) "Crystal structures of a template-independent DNA polymerase: murine terminal deoxynucleotidyltransferase", The European Molecular Biology Organization Journal, vol. 21, No. 3, pp. 427-439.

Diviacco, et al., (1992) "A novel procedure for quantitative polymerase chain reaction by coamplification of competitive templates", Gene, vol. 122, pp. 313-320.

Ferrero, et al., (2000) "Chemoenzymatic Transformations in Nucleoside Chemistry", Monatshefte fur Chemie, vol. 131, pp. 585-616.

Freeman, et al., (1999) "Quantitative RT-PCR: Pitfalls and Potential", Biotechniques, vol. 26, pp. 112-126.

Grantham, (1974) "Amino Acid Difference Formula to Help Explain Protein Evolution", Science, vol. 185, pp. 862-864.

Greenberg, et al., (1994) "Cleavage of Oligonucleotides from Solid-Phase Supports Using o-Nitrobenzyl Photochemistry", Journal Organic Chemistry, vol. 59, pp. 746-753.

Gulliksen, et al., (2004) "Real-Time Nucleic Acid Sequence-Based Amplification in Nanoliter Volumes", Analytical Chemistry, vol. 76, No. 1, pp. 9-14.

Guo, et al., (2008) "Four-color DNA sequencing with 3'-O-modififed nucleotide reversible terminators and chemically cleavable fluorescent dideoxynucleotides", Proceedings of the National Academy of Sciences, vol. 105. No. 27, pp. 9145-9150.

Haeberle, et al., (2007) "Microfluidic platforms for lab-on-a-chip applications", Lab Chip, vol. 7, No. 9, pp. 1094-1110.

Holland, et al., (1991) "Detection of specific polymerase chain reaction product by utilizing the 5'-3' exonuclease activity of Thermus aquaticus", Proceedings of the National Academy of Sciences, vol. 88, pp. 7276-7280.

Holmes, et al., (1997) "Model Studies for New o-Nitrobenzyl Photolabile Linkers: Substituent Effects on the Rate of Photochemical Cleavage", Journal Organic Chemistry, vol. 62, pp. 2370-2380.

Jensen, et al., (2018) "Template-Independent Enzymatic Oligonucleotide Synthesis (TiEOS): Its History, Prospects, and Challenges", Biochemistry, vol. 57, No. 12, pp. 1821-1832.

Kahl et al., (1998) "High-Yielding Method for On-Column Derivatization of Protected Oligodeoxy-nucleotides and Its Application to the Convergent Synthesis of 5',3'-Bis-conjugates", Journal Organic Chemistry, vol. 63, pp. 4870-4871.

Kahl et al., (1999) "Solution-Phased Bioconjugate Synthesis Using Protected Oligonucleotides Containing 3'-Alkyl Carboxylic Acids", Journal Organic Chemistry, vol. 64, pp. 507-510.

Leone, et al., (1998) "Molecular beacon probes combined with amplification by NASBA enable homogeneous, real-time detection of RNA", Nucleic Acids Research, vol. 26, No. 9, pp. 2150-2155.

MacKay, et al., (2002) "Survey and Summary Real-time PCR in virology", Nucleic Acids Research, vol. 30, No. 6, pp. 1292-1305.

Mag, et al., (1991) "Synthesis and selective cleavage of an oligodeoxynucleotide containing a bridged internucleotide 5'-phosphorothioate linkage", Nucleic Acids Research, vol. 19, No. 7, pp. 1437-1441.

(56) References Cited

OTHER PUBLICATIONS

Mathews, et al., (2016) "Photo-cleavable Nucleotides for Primer Free Enzyme mediated DNA Synthesis", Organic & Biomolecular Chemistry, 14, pp. 8278-8288.
Meng, et al., (2006) "Design and Synthesis of a Photocleavable Fluorescent Nucleotide 3'-O-Allyl-dGTP-PC-Bodipy-FL-510 as a Reversible Terminator for DNA Sequencing by Synthesis", Journal Organic Chemistry, vol. 71, No. 8, pp. 3248-3252.
Metzker, et al., (1994) "Termination of DNA synthesis by novel 3'-modified-deoxyribonucleoside 5'-triphosphates", Nucleic Acids Research, vol. 22, No. 20, pp. 4259-4267.
Motea, et al., (2010) "Terminal Deoxynucleotidyl Transferase: The Story of a Misguided DNA Polymerase", Biochim Biophys Acta, vol. 1804, No. 5, pp. 1151-1166.
Polstra, et al., (2002) Development of real-time NASBA assays with molecular beacon detection to quantify mRNA coding for HHV-8 lytic and latent genes, BMC Infectious Diseases, 2:18, pp. 1-10.
Pon, (1993) "Solid-Phase Supports for Oligonucleotide Synthesis", Methods Molecular Biology, vol. 20, pp. 465-496.
Rasolonjatovo, et al., (1999) "Development of a new DNA sequencing method: 3'-Ester cleavage catalyzed by Taq DNA polymerase", Nucleosides & Nucleotides, vol. 18, No. 4&5, pp. 1021-1022.
Schmitz, et al., (1999) "Solid-Phase Enzymatic Synthesis of Oligonucleotides", Organic Letters, vol. 1, No. 11, pp. 1729-1731.
Shoemaker, et al., (1996) "Quantitative phenotypic analysis of yeast dreletion mutants using a highly parallel molecular bar-coding strategy", Nature Genetics, vol. 14, pp. 450-456.
Sia, et al., (2003) "Micofluidic devices fabricated in poly(dimethylsiloxane) for biological studies", Electrophoresis, 24, pp. 3563-3576.
Taunton-Rigby, et al., (1973) "Oligonucleotide Synthesis. III. 1 Enzymatically Removable Acyl Protecting Groups", The Journal of Organic Chemistry, vol. 38, No. 5, pp. 977-985.
Uemura, et al., (1989) "Regioselective Deprotection of 3' ,5'-O-Acylated Pyrimidine Nucleosides by Lipase and Esterase", Tetrahedron Letters, vol. 30, No. 29, pp. 3819-3820.
Unger, et al., (2000) "Monolithic Microfabricated Valves and Pumps by Multilayer Soft Lithography", Science, vol. 288, pp. 113-116.
Venkatesan, et al., (1996) "Improved Utility of Photolabile Solid Phase Synthesis Supports for the Synthesis of Oligonucleotides Containing 3'-Hydroxyl Termini", The Journal of Organic Chemistry, vol. 61, pp. 525-529.
Verma, et al., (1998) "Modified Oligonucleotides: Synthesis and Strategy for Users", Annual Reviews Biochemistry, 67, pp. 99-134.
Weusten, et al., (2002) "Principles of quantitation of viral loads using nucleic acid sequence-based amplification in combination with homogeneous detection using molecular beacons", Nucleic Acids Research, vol. 30, No. 6, e26, pp. 1-7.
Zimmerman, et al., (1996) "Technical Aspects of Quantitative Competitive PCR", Biotechniques, vol. 21, No. 2, pp. 268-279.
International Preliminary Report on Patentablity mailed on Mar. 23, 2020, for PCT Application No. PCT/EP2019/087048, filed on Dec. 26, 2019, 6 pages.
International Search Report and Written Opinion mailed on Mar. 23, 2020, for PCT Application No. PCT/EP2019/087048, filed on Dec. 26, 2019, 9 pages.
Altschul, S.F. et al. (2005). "Protein Database Searches Using Compositionally Adjusted Substitution Matrices," The FEBS Journal 272:5101-5109.
Altschul, S.F. et al. (Sep. 1, 1997). "Gapped BLAST and PSI-BLAST: A New Generation of Protein Database Search Programs," Nucleic Acids Res. 25(17):3389-3402.
Lehninger, A.L. (1975). "The Amino Acid Building Blocks of Proteins," Chapter 4 in Biochemistry, second ed., Worth Publishers, New York, pp. 73-75.

* cited by examiner

ONE POT SYNTHESIS OF SETS OF OLIGONUCLEOTIDES

Oligonucleotide synthesis is a foundation technology of the medical and biological sciences. The ready availability of inexpensive oligonucleotides over a range of concentrations and purity levels is important for a host of technologies, including large-scale DNA sequencing, DNA amplification and detection technologies, diagnostics, and the like.

Currently oligonucleotides are produced for such applications using chemical methods, such as the phosphoramidite method, which require harsh conditions that preclude in situ production of oligonucleotides for use in enzymatic processes, such as DNA amplification. Moreover, reagents used in such methods are environmentally hazardous and present handling and disposal issues.

It would be highly desirable, especially for a variety of DNA amplification techniques, if a DNA synthesis approach was available that permitted the ready manufacture of multiple oligonucleotides in or at the same reaction environment which could be used directly in amplification or other oligonucleotide-dependent assays without the need of cumbersome steps of base-deprotection, purification, and the like, or delays while waiting for a mail order shipment to arrive.

SUMMARY OF THE INVENTION

The invention is directed to methods and devices, including microfluidic devices, for synthesizing a plurality of oligonucleotides in a single reaction vessel.

In some embodiments, the invention is directed to methods for synthesizing a plurality of oligonucleotides and performing one or more oligonucleotide-based assays in the same reaction vessel, such methods comprising the following steps: (a) repeating in a reaction vessel cycles of (i) contacting under elongation conditions an initiator having a free 3'-hydroxyl or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until elongated fragments are formed each containing a plurality of oligonucleotides separated from one another and from the initiator by cleavable nucleotides; (b) cleaving the cleavable nucleotides to free at least one of the plurality of oligonucleotides; (c) adding reagents for the oligonucleotide-based assay; and (d) performing the oligonucleotide-based assay, such as a polymerase chain reaction (PCR).

In some embodiments, the invention is directed to methods of synthesizing a plurality oligonucleotides in the same reaction vessel comprising the steps of: (a) providing one or more supports with two or more populations of initiators wherein the initiators of each population are terminated by a cleavable linkage or a cleavable nucleotide having a population-specific 3'-O-blocking group removable by deblocking conditions orthogonal to the deblocking conditions of the 3'-O-blocking groups of every other population of initiators; (b) deblocking population-specific blocking groups of a population of initiators or elongated fragments to form initiators or elongated fragments having free 3'-hydroxyls; (c) contacting under elongation conditions the population of initiators or its elongated fragments having free 3'-hydroxyls with a 3'-O-blocked nucleoside triphosphate and a template-independent DNA polymerase so that the initiators or elongated fragments are elongated by incorporation of the 3'-O-blocked nucleoside triphosphate to form 3'-O-blocked elongated fragments; and (d) repeating steps (b) and (c) for each population of initiators until elongated fragments are formed having nucleotide sequences of the plurality of oligonucleotides. In some embodiments, the above methods further include steps of (e) deblocking the elongated fragments; and (f) cleaving the cleavable nucleotides or cleavable linkages to free the elongated fragments and/or the plurality of oligonucleotides. In some embodiments, the above methods further include the steps of (g) adding reagents for the oligonucleotide-based assay; and (h) performing the oligonucleotide-based assay.

In some variations of the above embodiments, steps (b) through (d) may be implemented for each of the different populations of initiators consecutively so that each of the oligonucleotides of the plurality are synthesized consecutively. In other variations of the above embodiments, the steps (b) through (d) may be implemented for each of the different populations of initiators alternatively so that each of the oligonucleotides of the plurality are synthesized in parallel.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

DETAILED DESCRIPTION OF THE INVENTION

Figure 1A:
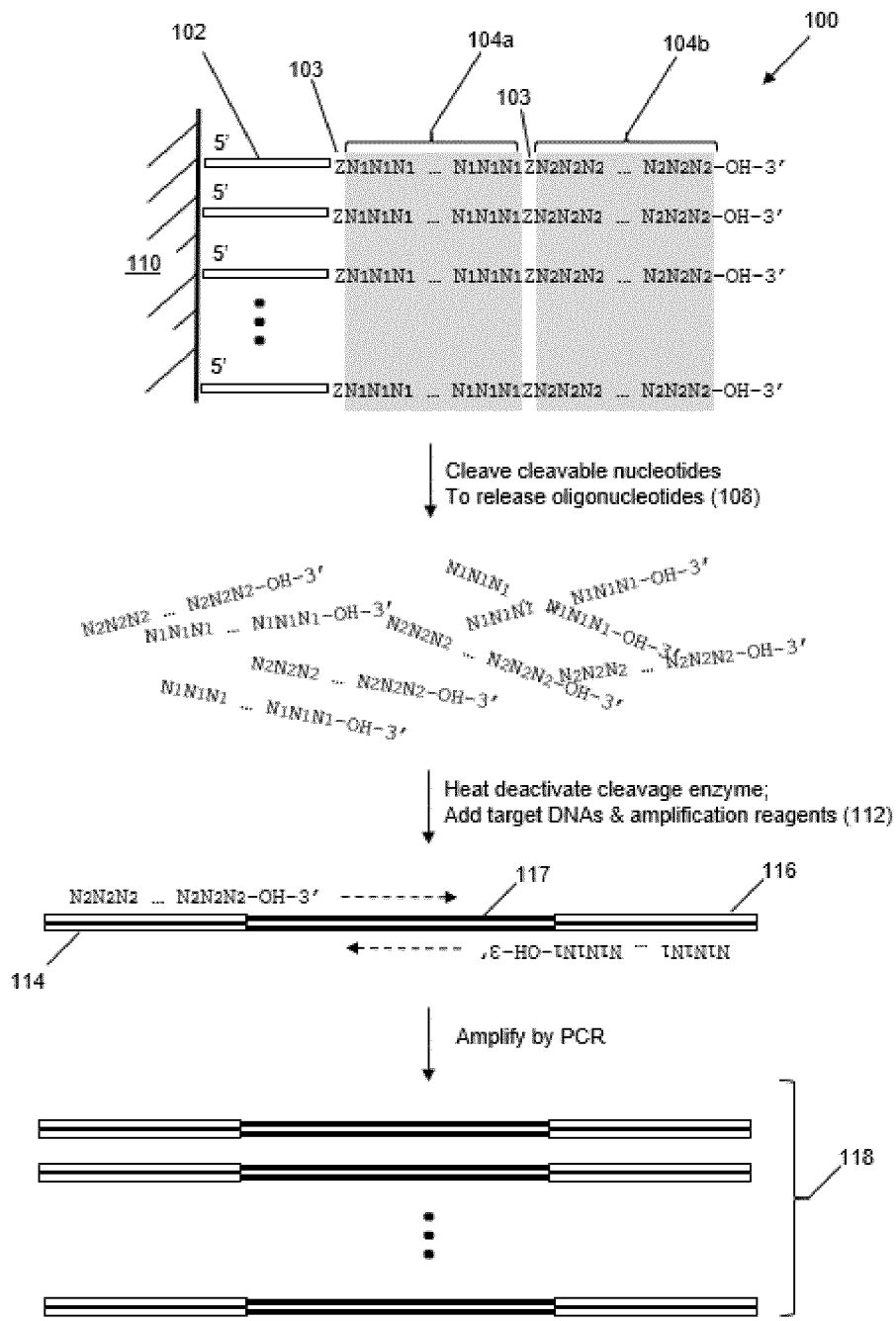
FIG. 1A illustrates one embodiment of enzymatic synthesis of multiple oligonucleotides in a single synthesis reaction employing a filter chamber.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

The invention is directed to synthesizing and using a plurality of oligonucleotides in a single reaction vessel. In some embodiments, the synthesized oligonucleotides are used directly in oligonucleotide-based reactions including, but not limited to, amplification reactions, such as, polymerase chain reaction (PCR), nucleic acid sequence-based amplification (NASBA), recombinase polymerase amplification (RPA), asymmetric PCR, nested PCR, quantitative PCR, and like techniques. In part the invention is a recognition that significant time and material efficiencies may be realized by enzymatically synthesizing required oligonucleotides and running oligonucleotide-based assays in the same reaction vessel. Such time and material efficiencies are not available for chemically synthesized oligonucleotides.

Figure 1B:
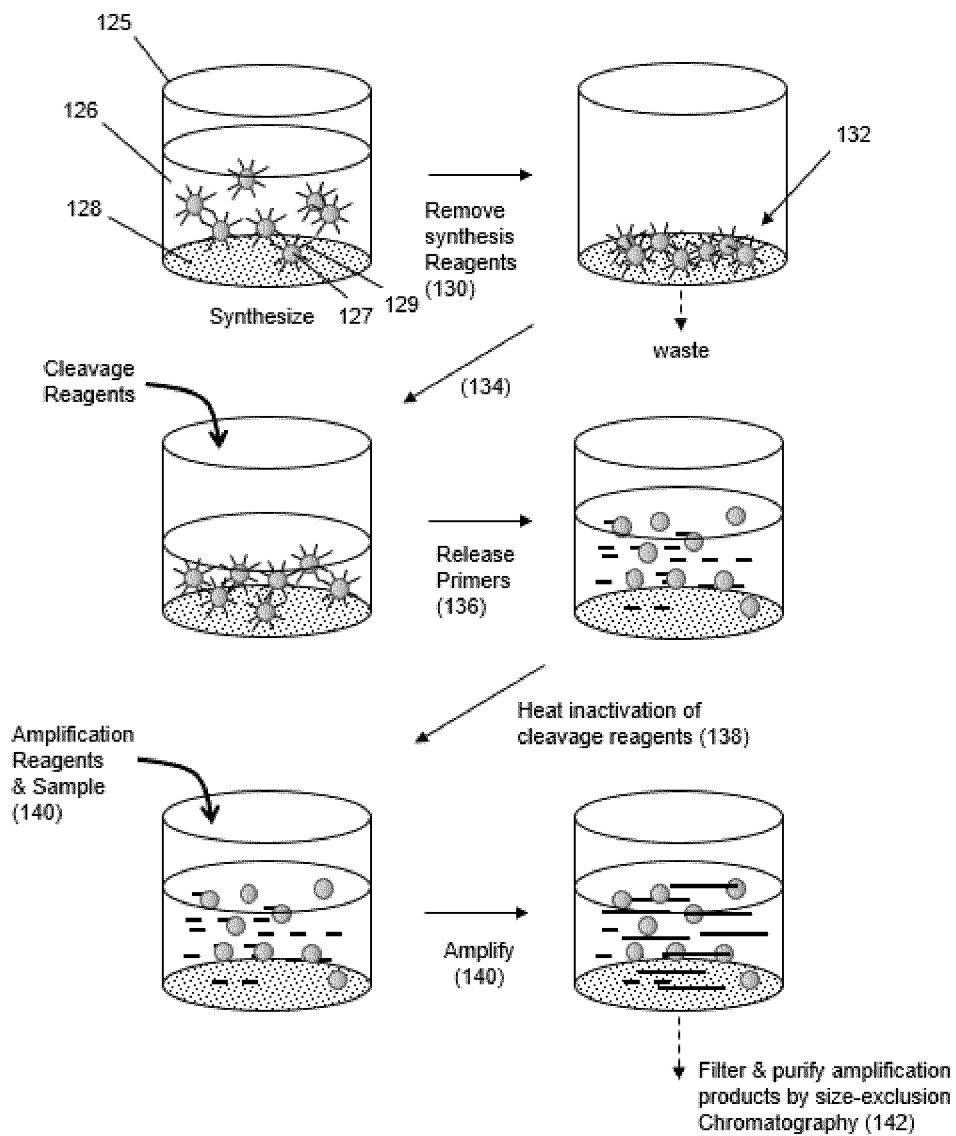
FIG. 1B illustrates one implementation of the embodiment of FIG. 1A.

An exemplary embodiment of the invention is illustrated in FIGS. 1A and 1B. As discussed more fully below, enzymatic synthesis of oligonucleotides with template-free polymerases, such as terminal deoxynucleotidyl transferase (TdT) requires a starting oligonucleotide referred to as an initiator. Thus, in this example, initiators (102) are attached by their 5' ends to solid support (110) using conventional techniques, for example, as disclosed in Hermanson (cited above), or by hybridizing to complementary oligonucleotides attached by their 3' ends. The repeated addition of nucleotides in a desired sequence proceeds as described below until the synthesis products (100) containing a plurality of desired oligonucleotides are obtained. In this embodiment, each desired oligonucleotide (104a and 104b) has a cleavable nucleotide "Z" (103) adjacent to its 5' end. An exemplary cleavable nucleotide is deoxyuridine which may be cleaved by treatment with uracil DNA-glycosylase (UDG) to excise uracil from the nucleotide followed by treatment with an AP endonuclease, such as endonuclease VIII, to excise the sugar leaving a 3'-hydroxyl on the downstream or proximal strand to the initiator, thereby leaving an extendable end on the downstream strand. Such cleavage releases (108) oligonucleotides (104a and 104b) for use in an oligonucleotide-based assay, such as PCR (112). In some embodiments, after release, the mixture containing the released oligonucleotides may be heated to deactivate the cleavage reagents, after which target nucleic acids and amplification reagents may be added for amplification. In this example, oligonucleotide (104b) is a forward primer annealing to primer binding site (114) and oligonucleotide (104a) is a reverse primer annealing to primer binding site (116) to amplify target polynucleotide (117) to produce amplicon (118).

FIG. 1B illustrates an embodiment for carrying out the invention in a reaction vessel comprising a filter chamber for selectively removing reagents. Reaction vessel (125) has filter wall (128) which is selected to permit, for example, vacuum driven removal of reaction solvent (126) from vessel (125), including dissolved salts, proteins, monomers, and the like, and retention of beads (127) and their attached polynucleotides (129). In this embodiment, initiators are attached to beads (127) which are suspended in reaction solvent (126). During synthesis initiators are elongated to form the elongation products illustrated in FIG. 1A. In each elongation cycle, initiators or previously elongated fragments are elongated by a single 3'-blocked nucleotide of a predetermined kind, after which the elongation reagents, which may include unincorporated protected dNTPs, polymerase, and polymerase reaction buffer, are removed by driving them through filter (128) by applying a vacuum. After synthesis of the polynucleotides containing the desired oligonucleotides is complete, final synthesis reagent (130) are removed through filter (128) by applying vacuum, leaving in vessel (125) beads (132) with the polynucleotides attached. Cleavage reagents for cleaving the cleavable nucleotides upstream each oligonucleotide (the Z's of FIG. 1A) are added (134) to reaction vessel (125) and incubated to release (136) the oligonucleotide primers from the beads, after which cleavage agent may be denatured or removed (138) if they could interfere with the subsequent amplification reaction. After release of the oligonucleotides and possible inactivation of cleavage reagents, amplification reagents and target polynucleotide-containing sample are added directly to reaction vessel (125) where amplification, e.g. via thermal cycling, takes place. In some embodiments, after amplification, amplicon sequences may be separated by size-exclusion chromatography using conventional techniques, e.g. Millipore Multiscreen® filter plate system (Billerica, MA).

Figure 2A:
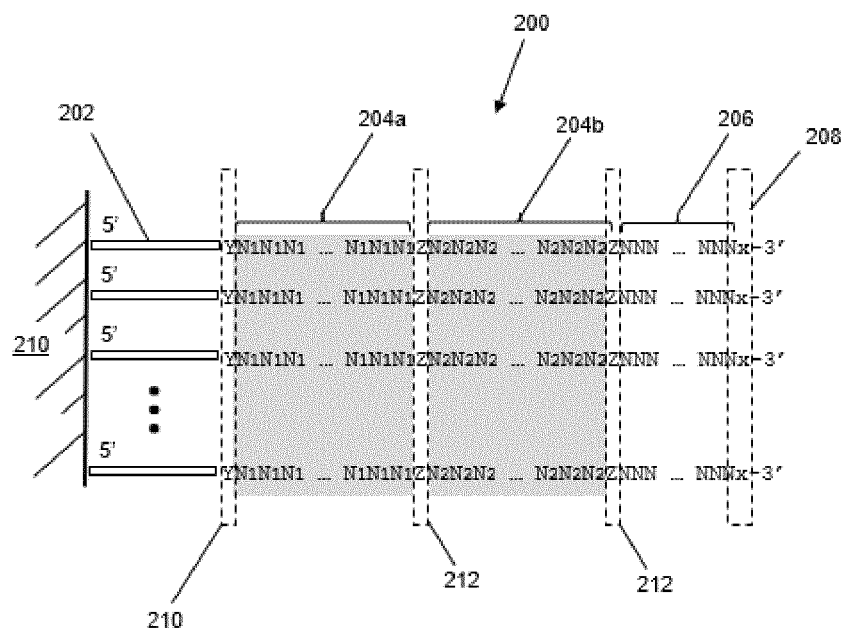
FIG. 2A illustrates another embodiment of enzymatic synthesis of multiple oligonucleotides in a single synthesis reaction employing beads.
Figure 2B:
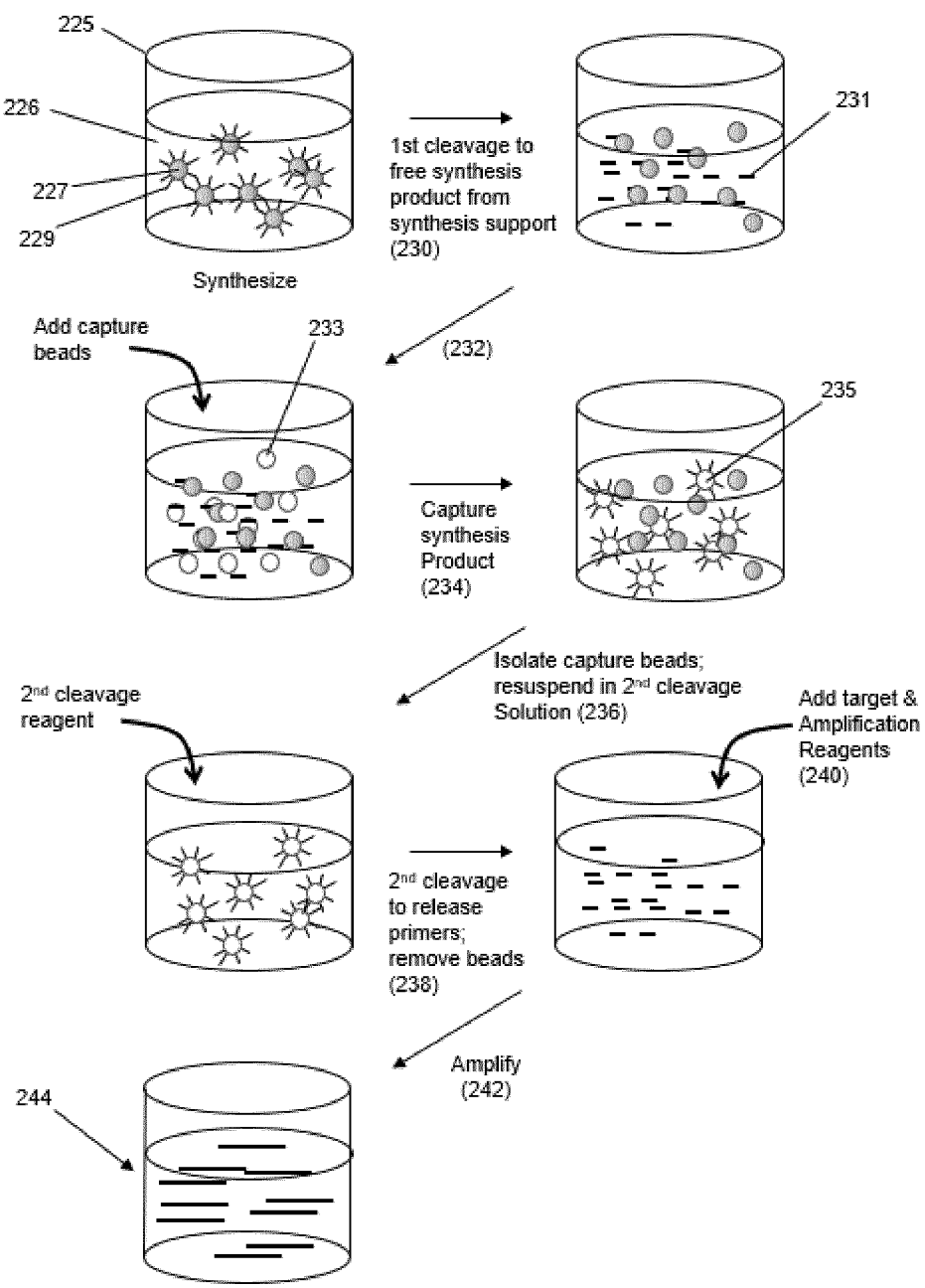
FIG. 2B illustrates one implementation of the embodiment of FIG. 2A.

FIG. 2A illustrates products from another embodiment of the invention. Initiator sequences (202) are attached to solid support (210) and polynucleotides (200) have been synthesized that comprise a plurality (two in this case) of oligonucleotides (204a and 204b) having at each end a cleavable nucleotide (210 and 212). In some embodiments, cleavable nucleotide (210) (shown as "Y") is cleaved under different conditions than that for cleaving the cleavable nucleotides (212) (shown as "Z"). Depending on the oligonucleotide-based assay, polynucleotides (200) may include segment (206), for example, to provide a complementary sequence for hybridizing to a capture oligonucleotide. In some embodiments, terminal nucleotides (208) include a capture moiety "x", which may be (for example) a biotin, or like moiety, that permits capture of polynucleotides (200) after they are release from solid support (210). For example, such a capture moiety may be added as the last nucleotide of the polynucleotide by incorporating a biotinylated dideoxynucleoside triphosphate, which after incorporation and release of the polynucleotide from a first solid support (as noted below) may be captured by a second solid support coated with streptavidin. In accordance with methods of the invention, after synthesis is completed, polynucleotides (200) are released from solid support (210) by cleaving cleavable nucleotide "Y" (210), after which they are captured by interaction of capture moiety "x" with a complementary agent, such as streptavidin, attached to a second solid support. The captured polynucleotides may be washed and cleavable nucleotides "Z" (212) may be cleaved to release oligonucleotides (204a and 204b) for use in an oligonucleotide-based assay. FIG. 2B further illustrates steps of synthesizing and processing of the products. Reaction vessel (225), unlike vessel (125) of FIG. 1B, does not have fluids removed by vacuum filtration, instead reagents are removed by aspiration and products are retained by being attached to beads, such as magnetic beads that may be excluded from fluids removed by aspiration by use of a magnet. Initiator sequence on beads (227) are extended with cycles of template-free incorporation of 3'-O-blocked dNTPs followed by deblocking, as described below, where each such cycle is accompanied by additions of reagents and removal of reagents by aspiration until a desired polynucleotide (229), or synthesis product, is completed. In this embodiment, after completion of synthesis, a first cleavage reaction is employed to cleave polynucleotides (229) from beads (227) so that they are released (231) into the reaction mixture (226). In some embodiments, such cleavage may be implemented by inserting a cleavable nucleotide between initiator and polynucleotide (229) as illustrated in FIG. 2A. In other embodiments, a wide variety scissile linkages may be employed, some of which may leave groups or modifications on the released polynucleotides, such as, modifications on the 3'-hydroxyl of the released polynucleotides. Released polynucleotides (231) are then captured via capture moiety "x" (208) or segment (206) by beads (233) added to vessel (225). Capture moieties (208) may include a wide range of conventional groups, such as biotin, and the like, which may be, or be attached to, a 3'-O-protection or blocking group. Alternatively, capture moieties may be attached to other locations on terminal nucleotide (208), such as a base, using conventional chemistries. In some embodiments, a capture moiety is selected so that it may be cleaved from the polynucleotides (thereby releasing the polynucleotides from capture beads (233)) to leave a free 3'-hydroxyl and without leaving modifications at other sites on the terminal nucleotide or elsewhere on the polynucleotides. In still other embodiments, polynucleotides (231) may be captured by capture beads (233) by way of hybridization to a capture oligonucleotide attached to beads (233) and complementary to segment (206). After capture (234) of released polynucleotides (231) by capture beads (235), capture beads (235) are isolated (236), for example, by retaining beads (235) by a magnetic field while reagents of vessel (225) are aspirated and replaced with a second cleavage reagent. Second cleavage reagent cleaves (238) cleavable nucleotides "Z" (212) to release the plurality of oligonucleotides, which may be directly used as primers or other components of an amplification reaction after amplification reagents and targets are added (240). After amplification (242), amplicon (244) is available in vessel (225) and may optionally be purified, for example, by size-exclusion chromatography.

Embodiments of the invention for synthesizing a plurality of oligonucleotides and performing one or more oligonucleotide-based assays, such as those described above, may be implemented by the following steps: (a) repeating in a reaction vessel cycles of (i) contacting under elongation conditions an initiator having a free 3'-hydroxyl or elongated fragments having free 3'-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until elongated fragments are formed each containing a plurality of oligonucleotides separated from one another and from the initiator by cleavable nucleotides or cleavable sites; (b) cleaving the cleavable nucleotides to free at least one of the plurality of oligonucleotides; (c) adding reagents for the oligonucleotide-based assay; and (d) performing the oligonucleotide-based assay. In some embodiments, the oligonucleotide-based assay may be a polymerase chain reaction (PCR) such that the step of adding further includes adding a polymerase, polymerase reaction buffer, nucleoside triphosphates, and such that one or more target polynucleotides has complementary segments to at least two of the oligonucleotides, so that sequences of the target polynucleotides between the complementary segments are amplified in the PCR. In some embodiments, the PCR is a multiplex PCR wherein a plurality of target polynucleotides are amplified. In some embodiments, such multiplex PCR is capable of amplifying a number of target polynucleotides in the range of from 2 to 1000; in another embodiment, such multiplex PCR is capable of amplifying a number of target polynucleotides in the range of from 2 to 100; such multiplex PCR is capable of amplifying a number of target polynucleotides in the range of from 2 to 10. In some embodiments, the step of cleaving comprises treating a cleavable nucleotides with an enzymatic activity and after cleavage deactivating the enzymatic. In some embodiments, the oligonucleotide-based assay is a nucleic acid sequence-based amplification (NASBA) and the step of adding further includes adding an RNA polymerase, an RNAse H, a reverse transcriptase, NASBA reaction buffer, nucleoside triphosphates, and one or more single stranded target nucleic acids at least one of which has complementary segment to at least one of the oligonucleotides so that sequences between the complementary segments are amplified in a NASBA reaction. In some embodiments, the initiators and elongation fragments are attached to a support and the step of cleaving leaves at least one of the oligonucleotides of the plurality attached to the support. In other embodiments, oligonucleotide-based assays may include nested PCR, asymmetric PCR, reverse-transcriptase PCR, quantitative PCR, or the like.

In the above and other embodiments employing supports for synthesis and amplifications, a wide variety of supports may be employed including solid supports, soluble polymer supports, membranes, and the like. In some embodiments, solid supports are employed for the synthesis steps; and in other embodiments, such solid supports are magnetic supports.

In some embodiments, such as illustrated in FIGS. 2A and 2B, more than one support may be used in the synthesis steps. For example, some embodiments employing more than one support may be implemented by the following steps: (a) providing an initiator attached to a first support in a reaction vessel, the initiator having a free 3'-hydroxyl; (b) repeating in the reaction vessel cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until elongated fragments are formed each containing a plurality of oligonucleotides separated from one another by cleavable nucleotides or cleavable linkages and each having a 3'-terminal capture moiety; (c) releasing the elongated fragments from the first support; (d) capturing the released elongated fragments on a second support by specific binding of the capture moiety to a complementary moiety on the second support; (e) cleaving the cleavable nucleotides or cleavable linkages to free the plurality of oligonucleotides; and (f) performing the oligonucleotide-based assay. As above, in some embodiments the oligonucleotide-based assay includes one or more polymerase chain reactions. In some embodiments, the step of capturing further includes removing reaction constituents of steps b) and c), for example, by washing, prior to performing the step of cleaving. In some embodiments, the step of cleaving the cleavable nucleotides or cleavable linkages produces oligonucleotides having free 3'-hydroxyls.

In some embodiments, elongated fragments, or polynucleotides, formed by the synthesis steps, for example, steps (a)-(d) above, are defined by the formula:

wherein:
SS$_1$ is a first support;
I is an initiator;
Z is a cleavable nucleotide or cleavable linkage;
[N]$_{ij}$ is an i$^{th}$ oligonucleotide having j nucleotides in the elongated fragment, or polynucleotide, containing a plurality of m oligonucleotides;
[N]$_k$ is an oligonucleotide of k nucleotides; and
x is said capture moiety attached to a nucleotide of [N]$_k$.

In some embodiments, j has a value in the range of from 4 to 50; or in the range of from 9 to 40. In some embodiments, i is 2 or greater; in other embodiments, i has a value in the range of from 2 to 10; in still other embodiments, i has a value in the range of from 2 to 4; in still other embodiments, i is 2 or 3. In some embodiments, x is a biotin.

Figure 3:
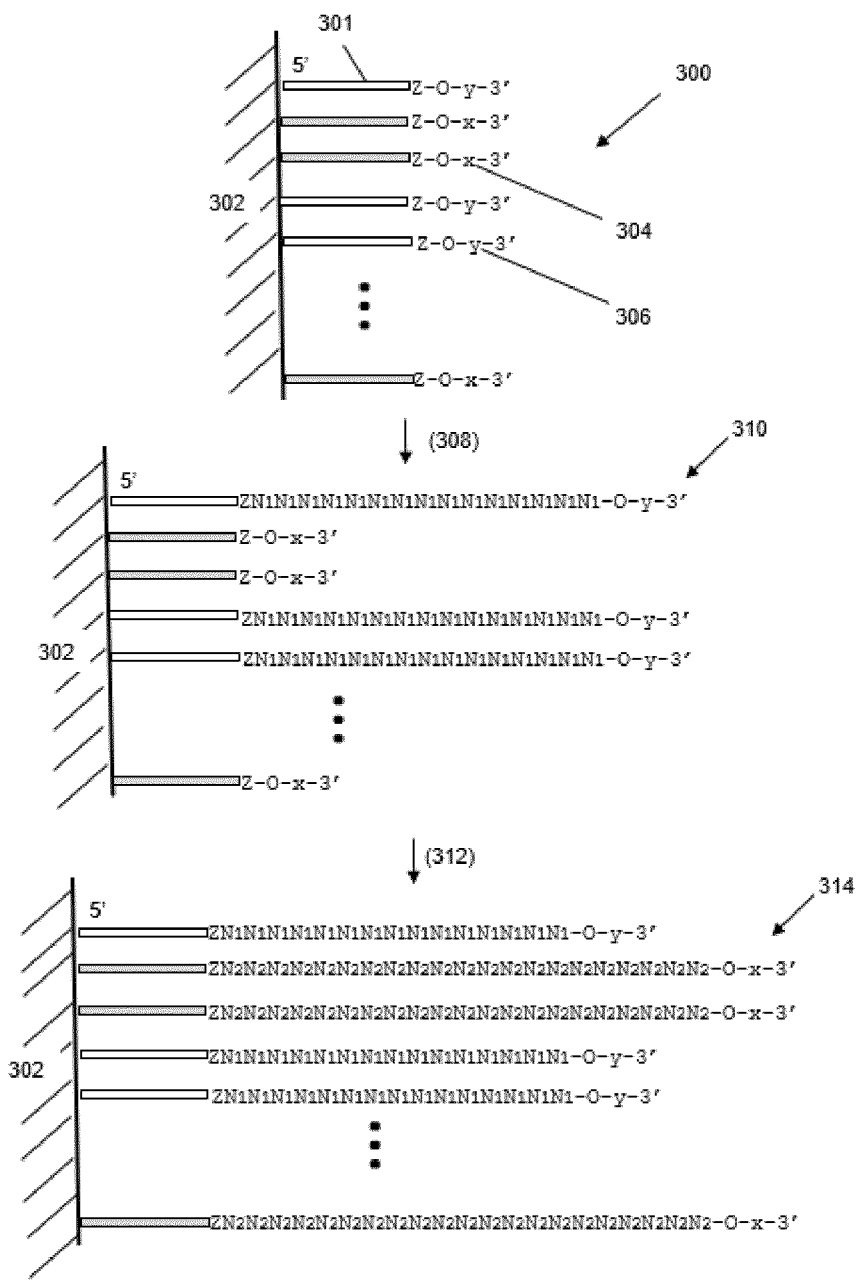
FIG. 3 illustrates an embodiment of the invention where a plurality of oligonucleotides are synthesized consecutively or alternatively on the same support.

FIGS. 2A-2B illustrate one embodiment in which a plurality of oligonucleotides are synthesized in series. That is, the different oligonucleotides of the plurality are each contained in series in a single polynucleotide, wherein after synthesis the polynucleotide is cleaved to produce the plurality. FIG. 3 illustrates embodiments wherein a plurality of oligonucleotides (300) in predetermined ratios are synthesized in parallel on one or more solid supports. One of ordinary skill would recognize that the invention includes conducting both serial and parallel synthesis in a single reaction vessel. Parallel synthesis with predetermined ratios of oligonucleotides is particularly applicable to techniques, such as, asymmetric PCR where one primer is provided in excess of the other primer in order to bias amplification to one strand of a target polynucleotide, or such as, quantitative PCR, where two primers are provided at one concentration and a probe is provided at a different concentration. In asymmetric PCRs, primer ratios may be 10:1 or greater; or in other embodiments, such ratios may be 100:1 or greater. These ratios may be implemented by attaching initiators for the different oligonucleotides in the desired ratio on a solid support using conventional chemical techniques, e.g. Hermanson (cited above). Alternatively, a plurality of populations of solid supports may be provided, such as different populations of beads each with a different initiator attached, so that desired ratios polynucleotides may be synthesized by disposing the corresponding ratio of different beads in a reaction vessel for synthesis. In some embodiments, different sets of 3'-O-blocked dNTPs may be employed, wherein for each different set the blocking groups are removed by orthogonal de-blocking conditions. Thus, if three different polynucleotides are to be synthesized in parallel, then blocking group 1 at the 3' end of the initiator of the first polynucleotide would be removed by de-blocking condition 1 that would not remove either blocking group 2 on the initiator used for the second polynucleotide or blocking group 3 on the initiator used with the third polynucleotide. The first polynucleotide would then be synthesized using 3'-blocking group 1-dNTPs. After the first polynucleotide is completed, de-blocking condition 2 would be used to remove blocking group 2 on the initiator for the second polynucleotide, which conditions would not remove blocking group 1 or blocking group 3. After such deblocking, the second polynucleotide would be synthesized using 3'-blocking group 2-dNTPs. After the second polynucleotide is completed, de-blocking condition 3 would be used to remove blocking group 3 from the initiator used for the third polynucleotide, which condition would not remove blocking group 1 or blocking group 2. The third polynucleotide would then be synthesized using 3'-blocking group 3-dNTPs. In some embodiments, the de-blocking conditions for one blocking group (say, blocking group 1) may de-block not only blocking group 1, but also blocking group 2. In such cases, the order of synthesis of the polynucleotides may be selected so that blocking group 2 is unaffected by the de-blocking condition 1. For example, in this case, where de-blocking condition 1 is not completely orthogonal, the second polynucleotide could be synthesized first and capped with a non-extendable moiety, after which the first and third polynucleotides could be synthesized.

In other embodiments, different blocking groups requiring orthogonal removal conditions are attached only to the initiators. Thus, in such embodiments, if three different polynucleotides are to be synthesized in parallel, then blocking group 1 at the 3' end of the initiator of the first polynucleotide would be removed with de-blocking condition 1 and the first polynucleotide would be synthesized using 3'-blocking group 1-dNTPs and capped with a non-extendable moiety. Next, blocking group 2 at the 3' end of the initiator for the second polynucleotide would be removed with de-blocking condition 2, after which the second polynucleotide would be synthesized using 3'-blocking group 1-dNTPs and capped with a non-extendable moiety. A like procedure would follow for the third polynucleotides. This embodiment has the advantage that only a single set of 3'-blocking group-dNTPs would have to be prepared.

One embodiment of such parallel synthesis is illustrated in FIG. 3 in which two different oligonucleotides are synthesized. Two different initiators (301) corresponding to the different oligonucleotides are attached to solid support (302) in a ratio that will result in the desired ratio of oligonucleotides being synthesized. In some embodiments, 3'-most nucleotide of the initiator may be a cleavable nucleotide. The different 3'-O-blocking groups are indicated as "x" (304) and "y" (306). The two oligonucleotides may be synthesized one at a time (as illustrated in FIG. 3) or they may be synthesized at the same time by alternating which oligonucleotide is elongated in every other elongation step. As shown in FIG. 3, oligonucleotides employing the "y" blocking group is elongated (308) in its entirety to produce elongation product (310) still having its 3'-hydroxyl blocked, after which (312) the oligonucleotide employing the "x" blocking group is elongated to produce elongation product (314). After both syntheses are complete, the two blocking groups may be removed and the oligonucleotides released from solid support (302) by cleaving cleavable nucleotide "Z". In some embodiments, blocking groups may be employed in which de-blocking conditions of one of the two blocking groups would remove both blocking groups. In such situations, the two blocking groups may still be used together provided that de-blocking steps be ordered so that the non-orthogonal de-blocking conditions are employed last.

Some embodiments of the invention, such as that of FIG. 3, for synthesizing a plurality of oligonucleotides in the same reaction vessel may be implemented by the following steps: (a) providing one or more supports with two or more populations of initiators wherein the initiators of each population are terminated by a cleavable linkage or a cleavable nucleotide having a population-specific 3'-O-blocking group removable by deblocking conditions orthogonal to the deblocking conditions of the 3'-O-blocking groups of every other population of initiators; (b) deblocking population-specific blocking groups of a population of initiators or elongated fragments to form initiators or elongated fragments having free 3'-hydroxyls; (c) contacting under elongation conditions the population of initiators or its elongated fragments having free 3'-hydroxyls with a 3'-O-blocked nucleoside triphosphate and a template-independent DNA polymerase so that the initiators or elongated fragments are elongated by incorporation of the 3'-O-blocked nucleoside triphosphate to form 3'-O-blocked elongated fragments; and (d) repeating steps (b) and (c) for each population of initiators until elongated fragments are formed having nucleotide sequences of the plurality of oligonucleotides. In some embodiments, the above methods further include steps of (e) deblocking the elongated fragments; and (f) cleaving the cleavable nucleotides or cleavable linkages to free the elongated fragments and/or the plurality of oligonucleotides. In some embodiments, the above methods further include the steps of (g) adding reagents for the oligonucleotide-based assay; and (h) performing the oligonucleotide-based assay. In some variations of the above embodiments, steps (b) through (d) may be implemented for each of the different populations of initiators consecutively so that each of the oligonucleotides of the plurality are synthesized consecutively. In other variations of the above embodiments, the steps (b) through (d) may be implemented for each of the different populations of initiators alternatively so that each of the oligonucleotides of the plurality are synthesized in parallel. In some embodiments of the above methods, the one or more supports are solid supports.

In some embodiments, methods of synthesizing a plurality of oligonucleotides in a single reaction vessel may be implemented by the following steps: (a) providing a plurality of different initiators attached to one or more supports, wherein at least one initiator of the plurality has free 3'-hydroxyls and wherein at least one initiator of the plurality has 3'-O-blocked terminal nucleotides; (b) synthesizing the plurality oligonucleotides by repeated cycles of template-free enzymatic nucleotide additions to each different initiator or its extension products of 3'-O-blocked nucleoside triphosphates, wherein the 3'-O-blocked nucleoside triphosphate has a blocking group that is removable under deblocking conditions orthogonal to deblocking conditions for removing blocking groups of other initiators of the plurality; and (c) releasing oligonucleotides from the extension products and the one or more solid supports. In some embodiments, the plurality of oligonucleotides is equal to or greater than said plurality of different initiators. That is, in some cases, each different oligonucleotide of a plurality may be synthesized from a different initiator, in which case the plurality of initiators is the same as the plurality of oligonucleotides. In other cases, one or more polynucleotides each comprising more than one oligonucleotide may be synthesized from different initiators, so that the plurality of oligonucleotides may be greater than the plurality of initiators. The different initiators may have different nucleotide sequences and/or lengths so long as their blocking groups may be removed by deblocking conditions that are orthogonal to the deblocking conditions used from the other initiators. Exemplary orthogonal deblocking conditions may include photo-cleavage, enzymatic cleavage, mild acid treatment, treatment with base, and the like, which can be used on the blocking groups on one kind of initiator with substantially affecting the blocking groups on the other kinds of initiator.

Template-Free Enzymatic Synthesis of Oligonucleotides

Figure 5:
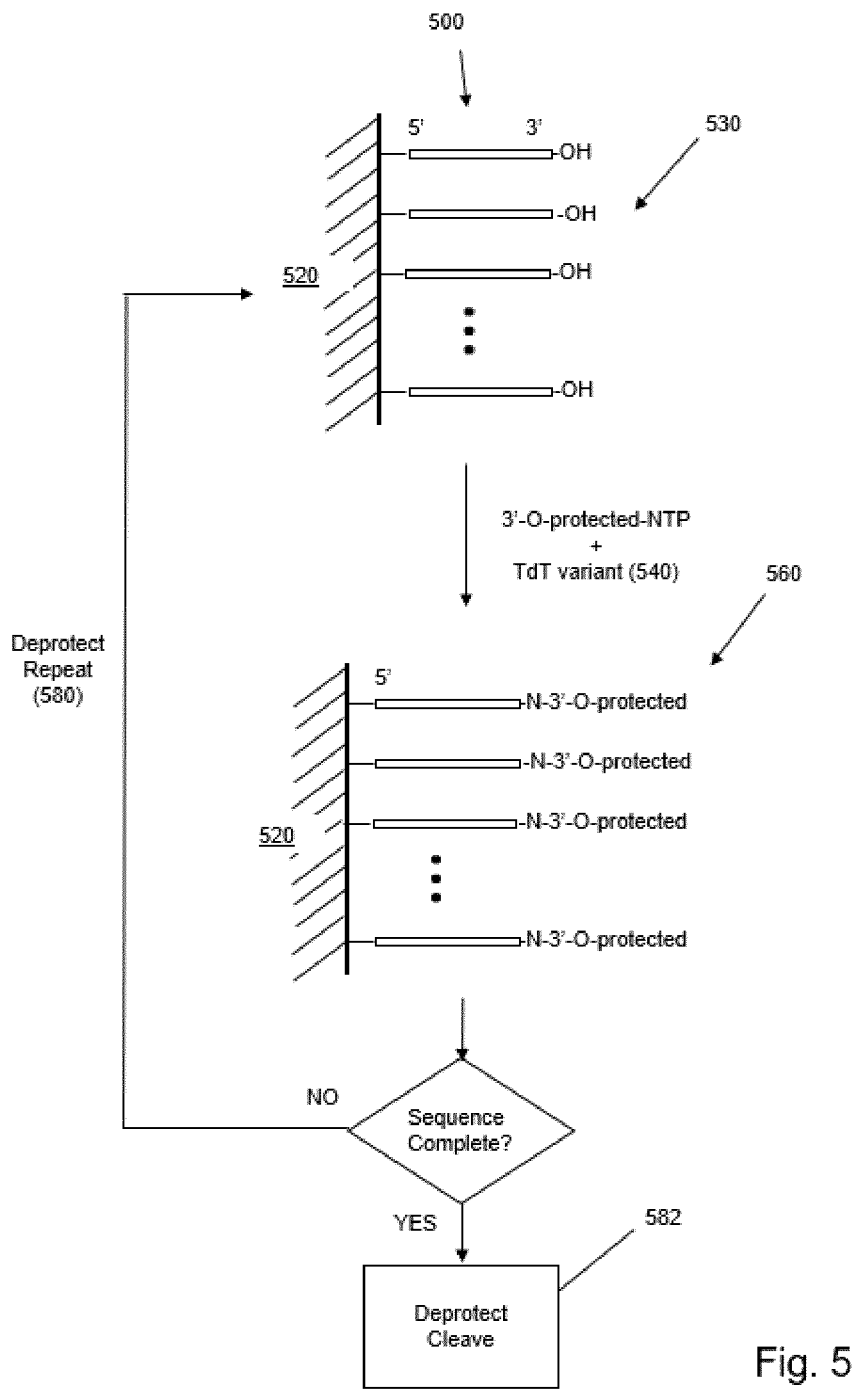
FIG. 5 illustrates basic steps for template-free enzymatic synthesis of polynucleotides of a predetermined sequence.

Generally, methods of template-free (or equivalently, "template-independent") enzymatic DNA synthesis comprise repeated cycles of steps, such as are illustrated in FIG. 5, in which a predetermined nucleotide is coupled to an initiator or growing chain in each cycle. The general elements of template-free enzymatic synthesis is described in the following references: Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

Initiator polynucleotides (500) are provided, for example, attached to solid support (520), which have free 3'-hydroxyl groups (530). To the initiator polynucleotides (500) (or elongated initiator polynucleotides in subsequent cycles) are added a 3'-O-protected-dNTP and a template-free polymerase, such as a TdT or variant thereof (e.g. Ybert et al, WO/2017/216472; Champion et al, WO2019/135007) under conditions (540) effective for the enzymatic incorporation of the 3'-O-protected-dNTP onto the 3' end of the initiator polynucleotides (500) (or elongated initiator polynucleotides). This reaction produces elongated initiator polynucleotides whose 3'-hydroxyls are protected (560). If the elongated sequence is not complete, then another cycle of addition is implemented (580). If the elongated initiator polynucleotide contains a competed sequence, then the 3'-O-protection group may be removed, or deprotected, and the desired sequence may be cleaved from the original initiator polynucleotide (582). Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. If the elongated initiator polynucleotide does not contain a completed sequence, then the 3'-O-protection groups are removed to expose free 3'-hydroxyls (530) and the elongated initiator polynucleotides are subjected to another cycle of nucleotide addition and deprotection.

As used herein, an "initiator" (or equivalent terms, such as, "initiating fragment," "initiator nucleic acid," "initiator oligonucleotide," or the like) usually refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20 nucleotides. In some embodiments, the initiating fragment is single-stranded. In alternative embodiments, the initiating fragment is double-stranded. In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

Returning to FIG. 5, in some embodiments, an ordered sequence of nucleotides are coupled to an initiator nucleic acid using a template-free polymerase, such as TdT, in the presence of 3'-O-protected dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a template-free polymerase in the presence of a 3'-O-protected nucleoside triphosphate to produce a 3'-O-protected extension intermediate; (c) deprotecting the extension intermediate to produce an extension intermediate with a free 3'-hydroxyl; and (d) repeating steps (b) and (c) until the polynucleotide is synthesized. (Sometimes the terms "extension intermediate" and "elongation fragment" are used interchangeably). In some embodiments, an initiator is provided as an oligonucleotide attached to a solid support, e.g. by its 5' end. The above method may also include washing steps after the reaction, or extension, step, as well as after the de-protecting step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

When the sequence of polynucleotides on a synthesis support includes reverse complementary subsequences, secondary intra-molecular or cross-molecular structures may be created by the formation of hydrogen bonds between the reverse complementary regions. In some embodiments, base protecting moieties for exocyclic amines are selected so that hydrogens of the protected nitrogen cannot participate in hydrogen bonding, thereby preventing the formation of such secondary structures. That is, base protecting moieties may be employed to prevent the formation of hydrogen bonds, such as are formed in normal base pairing, for example, between nucleosides A and T and between G and C. At the end of a synthesis, the base protecting moieties may be removed and the polynucleotide product may be cleaved from the solid support, for example, by cleaving it from its initiator.

3'-O-blocked dNTPs without base protection may be purchased from commercial vendors or synthesized using published techniques, e.g. U.S. Pat. No. 7,057,026; Guo et al, Proc. Natl. Acad. Sci., 105(27): 9145-9150 (2008); Benner, U.S. Pat. Nos. 7,544,794 and 8,212,020; International patent publications WO2004/005667, WO91/06678; Canard et al, Gene (cited herein); Metzker et al, Nucleic Acids Research, 22: 4259-4267 (1994); Meng et al, J. Org. Chem., 14: 3248-3252 (3006); U.S. patent publication 2005/037991. 3'-O-blocked dNTPs with base protection may be synthesized as described below.

When base-protected dNTPs are employed the above method of FIG. 5 may further include a step (e) removing base protecting moieties, which in the case of acyl or amidine protection groups may (for example) include treating with concentrated ammonia.

The above method may also include capping step(s) as well as washing steps after the reacting, or extending, step, as well as after the deprotecting step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments, reaction conditions for an extension or elongation step may comprising the following: 2.0 µM purified TdT; 125-600 µM 3'-O-blocked dNTP (e.g. 3'-O—$NH_2$-blocked dNTP); about 10 to about 500 mM potassium cacodylate buffer (pH between 6.5 and 7.5) and from about 0.01 to about 10 mM of a divalent cation (e.g. $CoCl_2$ or $MnCl_2$), where the elongation reaction may be carried out in a 50 µL reaction volume, at a temperature within the range RT to 45° C., for 3 minutes. In embodiments, in which the 3'-O-blocked dNTPs are 3'-O—$NH_2$-blocked dNTPs, reaction conditions for a deblocking step may comprise the following: 700 mM $NaNO_2$; 1 M sodium acetate (adjusted with acetic acid to pH in the range of 4.8-6.5), where the deblocking reaction may be carried out in a 50 µL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: Benner, U.S. Pat. Nos. 7,544,794 and 8,212,020; 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments. It is understood that other blocking group pairs, or groups containing more than two, may be available for use in these embodiments of the invention.

| | |
|---|---|
| 3'-O—NH2 | 3'-O-azidomethyl |
| 3'-O—NH2 | 3'-O-allyl |
| 3'-O—NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM MgCl$_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoester/nucleotidyl-2',3'-cyclic phosphate, nuclcotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte fur Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

wherein —Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula=C(R''')$_2$ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')$_2$—F, the F is exchanged for OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, -Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA).

In a further embodiment, the 3'-blocked nucleotide triphosphate is blocked by either a 3'-O-azidomethyl, 3'-O—NH$_2$ or 3'-O-allyl group.

In still other embodiments, 3'-O-blocking groups of the invention include 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), and 3'-O-propargyl.

In some embodiments, 3'-O-protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

In some embodiments, enzymatic synthesis methods employ TdT variants that display increased incorporation activity with respect to 3'-O-modified nucleoside triphosphates. For example, such TdT variants may be produced using techniques described in Champion et al, U.S. patent Ser. No. 10/435,676, which is incorporated herein by reference. In some embodiments, a TdT variant is employed having an amino acid sequence at least 60 percent identical to SEQ ID NO: 2 and a substitution at a first arginine at position 207 and a substitution at a second arginine at position 325, or functionally equivalent residues thereof. In some embodiments, a terminal deoxynucleotidyl transferase (TdT) variant is employed that has an amino acid sequence at least sixty percent identical to an amino acid sequence selected from SEQ ID NO: 2, 3, 4, 5, 6, 7, 8, 9, 10, 11, 12, 13, 14 or 15 with a substitution of arginine ("first arginine") at position 207 with respect to SEQ ID NOs 2, 3, 4, 6, 7, 9, 12 and 13, at position 206 with respect to SEQ ID NO 5, at position 208 with respect to SEQ ID NOs 8 and 10, at position 205 with respect to SEQ ID NO 11, at position 216 with respect to SEQ ID NO 14 and at position 210 with respect to SEQ ID NO 15; and a substitution of arginine ("second arginine") at position 325 with respect to SEQ ID NOs 2, 9 and 13, at position 324 with respect to SEQ ID NOs 3 and 4, at position 320 with respect to SEQ ID NO 320, at position 331 with respect to SEQ ID NOs 6 and 8, at position 323 with respect to SEQ ID NO 11, at position 328 with respect to SEQ ID NOs 12 and 15, and at position 338 with respect to SEQ ID NO 14; or functionally equivalent residues thereof; wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100.

In regard to (ii), such 3'-O-modified nucleotide may comprise a 3'-O—$NH_2$-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the above TdT variants have substitutions at the first and second arginines as shown in Table 1.

TABLE 1

Examples of TdT variants

| SEQ ID NO | Substitutions | | | | |
|---|---|---|---|---|---|
| 1 | M192R/Q | C302G/R | R336L/N | R454P/N/A/V | E457N/L/T/S/K |
| 2 | M63R/Q | C173G/R | R207L/N | R325P/N/A/V | E328N/L/T/S/K |
| 3 | M63R/Q | C173G/R | R207L/N | R324P/N/A/V | E327N/L/T/S/K |
| 4 | M63R/Q | C173G/R | R207L/N | R324P/N/A/V | E327N/L/T/S/K |
| 5 | — | C172G/R | R206L/N | R320P/N/A/V | — |
| 6 | M63R/Q | C173G/R | R207L/N | R331P/N/A/V | E334N/L/T/S/K |
| 7 | M63R/Q | C173G/R | R207L/N | — | E328N/L/T/S/K |
| 8 | — | C174G/R | R208L/N | R331P/N/A/V | E334N/L/T/S/K |
| 9 | M73R/Q | C173G/R | R207L/N | R325P/N/A/V | E328N/L/T/S/K |
| 10 | M64R/Q | C174G/R | R208L/N | — | E329N/L/T/S/K |
| 11 | M61R/Q | C171G/R | R205L/N | R323P/N/A/V | E326N/L/T/S/K |
| 12 | M63R/Q | C173G/R | R207L/N | R328P/N/A/V | E331N/L/T/S/K |
| 13 | — | C173G/R | R207L/N | R325P/N/A/V | E328N/L/T/S/K |
| 14 | M63R/Q | C182G/R | R216L/N | R338P/N/A/V | E341N/L/T/S/K |
| 15 | M66R/Q | C176G/R | R210L/N | R328P/N/A/V | E331N/L/T/S/K |

In some embodiments, further TdT variants for use with methods of the invention include one or more of the further substitutions of methionine, cysteine or glutamic acid, as shown in Table 1.

Further specific TdT variants that may be used in methods of the invention are set forth in Table 2. Each of the TdT variants DS1001 through DS1018 of Table 2 comprises an amino acid sequence at least 60 percent identical to SEQ ID NO 2 and comprises the substitutions at the indicated positions. In some embodiments, TdT variants DS1001 through DS1018 comprises an amino acid sequence at least 80 percent identical to SEQ ID NO 2 and comprises the substitutions at the indicated positions; in some embodiments, TdT variants DS1001 through DS1018 comprises an amino acid sequence at least 90 percent identical to SEQ ID NO 2 and comprises the substitutions at the indicated positions; in some embodiments, TdT variants DS1001 through DS1018 comprises an amino acid sequence at least 95 percent identical to SEQ ID NO 2 and comprises the substitutions at the indicated positions; in some embodiments, TdT variants DS1001 through DS1018 comprises an amino acid sequence at least 97 percent identical to SEQ ID NO 2 and comprises the substitutions at the indicated positions; in some embodiments, TdT variants DS1001 through DS1018 comprises an amino acid sequence at least 98 percent identical to SEQ ID NO 2 and comprises the substitutions at the indicated positions; in some embodiments, TdT variants DS1001 through DS1018 comprises an amino acid sequence at least 99 percent identical to SEQ ID NO 2 and comprises the substitutions at the indicated positions.

TABLE 2

Specific TdT Variants for Use with Methods of the Invention

| | |
|---|---|
| DS1001 (TH M27) | A17V + L52F + M63R + A108V + C173G + R207L + K265T + G284P + E289V + R325P + E328N + R351K |
| DS1002 (M44) | A17V + Q37E + D41R + L52F + G57E + M63R + S94R + G98E + A108V + S119A + L131R + S146E + Q149R + C173G + R207L + K265T + G284P + E289V + R325P + Q326F + E328N + H337D + R351K + W377R |
| DS1003 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1004 (M45) | A17V + Q37E + D41R + L52F + G57E + M63R + S94R + G98E + A108V + S146E + Q149R + C173G + F193Y + V199M + M201V + R207L + K265T + G284P + E289V + R325A + Q326F + E328N + R351K |
| DS1005 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1006 (M46) | L52F + A108V + R351K + A17V + Q37E + D41R + G57E + C59R + L60D + M63R + S94R + G98E + S119A + L131R + S146E + Q149R + C173G + R207L + K265T + G284P + E289V + R325A + Q326F + E328N |
| DS1007 (M47) | L52F + A108V + R351K + A17V + Q37E + D41R + G57E + C59R + L60D + M63R + S94R + G98E + K118Q + S119A + L131R + S146E + Q149R + C173G + R207L + K265T + G284P + E289V + R325A + Q326F + E328N + W377R |
| DS1008 | A17V + Q37E + D41R + L52F + G57E + C59R + L60D + M63R + S94R + G98E + A108V + S119A + L131R + S146E + Q149R + C173G + R207L + F259S + Q261L + G284P + E289V + R325A + Q326F + E328N + R351K + W377R |
| DS1009 (MS 13-34) | A17V + D41R + L53F + G57E + C59R + L60D + M63R + S94R + G98E + K118Q + S119A + L131R + S146E + Q149R + C173G + R207L + K265T + G284P + E289V + R325A + Q326F + R351K + W377R |
| DS1010 (MS 34-1) | A17V + D41R + L52F + G57E + C59R + L60D + M63R + S94R + G98E + A108V + S119A + L131R + S146E + Q149R + R207L + K265T + G284P + E289V + R325A + Q326F + R351K |
| DS1011 | A17V + D41R + L53F + G57E + C59R + L60D + M63R + S94R + G98E + K118Q + S119A + L131R + S146E + Q149R + C173G + R207L + K265T + G284P + E289V + Q326F + R351K + W377R |
| DS1012 (M48) | A17V + Q37E + D41R + L52F + G57E + C59R + L60D + M63R + S94R + G98E + A108V + S119A + L131R+ S146E + Q149R + C173G + R207L + F259S + Q261L, G284P + E289V + R325A + Q326F + E328N + R351K + W377R |
| DS1013 | A17V + Q37E + D41R + L52F + G57E + M63R + S94R + G98E + A108V + S146E + Q149R + C173G + R207L + K265T + G284P + E289V + R325A + Q326F + E328N + R351K |
| DS1014 (M49) | A17V + Q37E + D41R + L52F + G57E + C59R + L60D + M63R + S94R + G98E + A108V + S119A + L131R + S146E + Q149R + C173G + R207L + E257D + F259S + K260R + Q261L + G284P + E289V + R325A + Q326F + E328N + R351K + W377R |
| DS1015 | A17V + Q37E + D41R + L52F + G57E + C59R + L60D + M63R + S94R + G98E + A108V + S119A + L131R + S146E + Q149R + C173G + F193Y + V199M + M201V + R207L + E257D + F259S + K260R + Q261L + G284P + E289V + R325A + Q326F + E328N + R351K + W377R |
| DS1016 TH c2_5 | A17V + D41R + L52F + G57E + M63R + S94R + G98E + A108V + S146E + Q149R + C173G + M184T + R207L + K209H + G284L + E289A + R325V + E328K + R351K |
| DS1017 (M27) | A17V + L52F + G57E + M63R + A108V + C173G + R207L + K265T + G284P + E289V + R325P + E328N + R351K |
| DS1018 (M60) | A17V + L32T + Q37R + D41R + L52F + G57E + C59R + L60D + M63R + S67A + S94R + G98E + A108V + S119A + L131R + S146E + Q149R + V171A + S172E + C173R + V182I + S183E + R207L + K209H + M210K + T211I + E223G + A224P + E228D + Q261L + G284P + E289V + R325A + Q326F + E328N + R351K + D372E |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 3A.

TABLE 3A

Synonymous Sets of Amino Acids I

| Amino Acid | Synonymous Set |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 3B.

TABLE 3B

Synonymous Sets of Amino Acids II

| Amino Acid | Synonymous Set |
| --- | --- |
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Cleavable Linkages and Nucleotides

A wide variety of cleavable linkages, or more particularly, cleavable nucleotides, may be used with embodiments of the invention. As used herein, the term "cleavable site" refers to a nucleotide or backbone linkage of a single stranded nucleic acid sequence that can be excised or cleaved under predetermined conditions, thereby separating the single stranded nucleic acid sequence into two parts. In some embodiments, a step of cleaving a cleavable nucleotide or a cleavable linkage leaves a free 3'-hydroxyl on a cleaved strand, thereby, for example permitting the cleaved strand to be extended by a polymerase. Cleaving steps may be carried out chemically, thermally, enzymatically or by light-based cleavage. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage by glycosylases and/or endonucleases may require a double stranded DNA substrate In some embodiments, cleavable nucleotides include nucleotides comprising base analogs cleavable by endonuclease III which include, but are not limited to, urea, thymine glycol, methyl tartonyl urea, alloxan, uracil glycol, 6-hydroxy-5,6-dihydrocytosine, 5-hydroxyhydantoin, 5-hydroxycytocine, trans-1-carbamoyl-2-oxo-4,5-dihydrooxyimidazolidine, 5,6-dihydrouracil, 5-hydroxycytosine, 5-hydroxyuracil, 5-hydroxy-6-hydrouracil, 5-hydroxy-6-hydrothymine, 5,6-dihydrothymine. In some embodiments, cleavable nucleotides include nucleotides comprising base analogs cleavable by formamidopyrimidine DNA glycosylase which include, but are not limited to, 7,8-dihydro-8-oxoguanine, 7,8-dihydro-8-oxoinosine, 7,8-dihydro-8-oxoadenine, 7,8-dihydro-8-oxonebularine, 4,6-diamino-5-formamidopyrimidine, 2,6-diamino-4-hydroxy-5-formamidopyrimidine, 2,6-diamino-4-hydroxy-5-N-methylformamidopyrimidine, 5-hydroxycytosine, 5-hydroxyuracil. In some embodiments, cleavable nucleotides include nucleotides comprising base analogs cleavable by hNeil 1 which include, but are not limited to, guanidinohydantoin, spiroiminodihydantoin, 5-hydroxyuracil, thymine glycol. In some embodiments, cleavable nucleotides include nucleotides comprising base analogs cleavable by thymine DNA glycosylase which include, but are not limited to, 5-formylcytosine and 5-carboxycytosine. In some embodiments, cleavable nucleotides include nucleotides comprising base analogs cleavable by human alkyladenine DNA glycosylase which include, but are not limited to, 3-methyladenine, 3-methylguanine, 7-methylguanine, 7-(2-chloroehyl)-guanine, 7-(2-hydroxyethyl)-guanine, 7-(2-ethoxyethyl)-guanine, 1,2-bis-(7-guanyl)ethane, 1,$N^6$-ethenoadenine, 1,$N^2$-ethenoguanine, $N^2$,3-ethenoguanine, $N^2$,3-ethanoguanine, 5-formyluracil, 5-hydroxymethyluracil, hypoxanthine. In some embodiments, cleavable nucleotides include 5-methylcytosine cleavable by 5-methylcytosine DNA glycosylase.

Exemplary chemically cleavable internucleotide linkages for use in the methods described herein include, for example, —cyano ether, 5'-deoxy-5'-aminocarbamate, 3'deoxy-3'-aminocarbamate, urea, 2'cyano-3',5'-phosphodiester, 3'-(S)-phosphorothioate, 5'-(S)-phosphorothioate, 3'-(N)-phosphoramidate, 5'-(N)-phosphoramidate, —amino amide, vicinal diol, ribonucleoside insertion, 2'-amino-3',5'-phosphodiester, allylic sulfoxide, ester, silyl ether, dithioacetal, 5'-thio-furmal, —hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include —cyano ether, 5'-deoxy-5'-aminocarbamate, 3'-deoxy-3'-aminocarbamate, urea, 2'-cyano-3',5'-phosphodiester, 2'-amino-3',5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An —aminoamide internucleotide bond is cleavable by treatment with isothiocyanate, and titanium may be used to cleave a 2'-amino-3',5'-phosphodiester-O-ortho-benzyl internucleotide bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642

Further cleavable linkages are disclosed in the following references: Pon, R., Methods Mol. Biol. 20:465-496 (1993); Verma et al., Ann. Rev. Biochem. 67:99-134 (1998); U.S. Pat. Nos. 5,739,386, 5,700,642 and 5,830,655; and U.S. Patent Publication Nos. 2003/0186226 and 2004/0106728, Urdea et al, U.S. Pat. No. 5,367,066.

The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

Synthesis and cleavage conditions of chemically cleavable oligonucleotides are described in U.S. Pat. Nos. 5,700,642 and 5,830,655. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide. In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide, which may (if desired) be removed by a phosphatase.

In some embodiments, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., J. Org. Chem. 61:525-529 (1996), Kahl et al., J. Org. Chem. 64:507-510 (1999), Kahl et al., J. Org. Chem. 63:4870-4871 (1998), Greenberg et al., J. Org. Chem. 59:746-753 (1994), Holmes et al., J. Org. Chem. 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially.

In some embodiments, ribonucleotides may be employed as cleavable nucleotides, wherein a cleavage step may be implemented using a ribonuclease, such as RNase H. In other embodiments, cleavage steps may be carried out by treatment with a nickase.

Kits

The invention includes kits for carrying out methods of the invention. In some embodiments, kits of the invention are for synthesizing in series a plurality of oligonucleotides for implementing a PCR, wherein the kits include 3'-O-blocked cleavable nucleoside triphosphates for inserting cleavable nucleotides at predetermined locations of a polynucleotide product. In some embodiments, such kits further include a solid support with an initiator attached. In further embodiments, such kits include a plurality of solid supports wherein each different solid support of the plurality has an initiator attached that has a different 3'-O-blocking group attached such that each different blocking group is removable by orthogonal de-blocking conditions. In further embodiments, such kits include a solid support with a plurality of different initiators attached in predetermined ratios, wherein each different initiator has a different 3'-O-blocking group attached such that each different blocking group is removable by orthogonal de-blocking conditions. In each of the foregoing kits, the different initiators may have nucleotide sequences that are the same or different.

In some embodiments of the foregoing kits, solid supports and initiators are provided for practicing asymmetric PCR so that the plurality of initiators is two and the predetermined ratio of different initiators is at least 10:1; and in other embodiments, at least 100:1. In some embodiments of the foregoing kits, solid supports and initiators are provided for practicing nested PCR so that when polynucleotide products are synthesized two sets of forward and reverse primers may be released for carrying out amplification reactions. In one form of this embodiment, two solid supports are provided wherein on one solid support two primers are synthesized serially and on the other solid support two primers are synthesized serially, and wherein initiators on the different solid supports have different 3'-O-blocking groups that may be removed by orthogonal de-blocking conditions. In another form of these embodiments, one or more kinds of 3'-O-blocked cleavable nucleoside triphosphates are provided In some embodiments, kits provide solid supports and 3'-O-blocked cleavable nucleoside triphosphates for implementing nucleic acid sequence-based amplification (NASBA), recombinase polymerase amplification (RPA), or quantitative PCR.

Example 1: Parallel Synthesis of Primers and Taqman Probe for qPCR

Figure 4A:
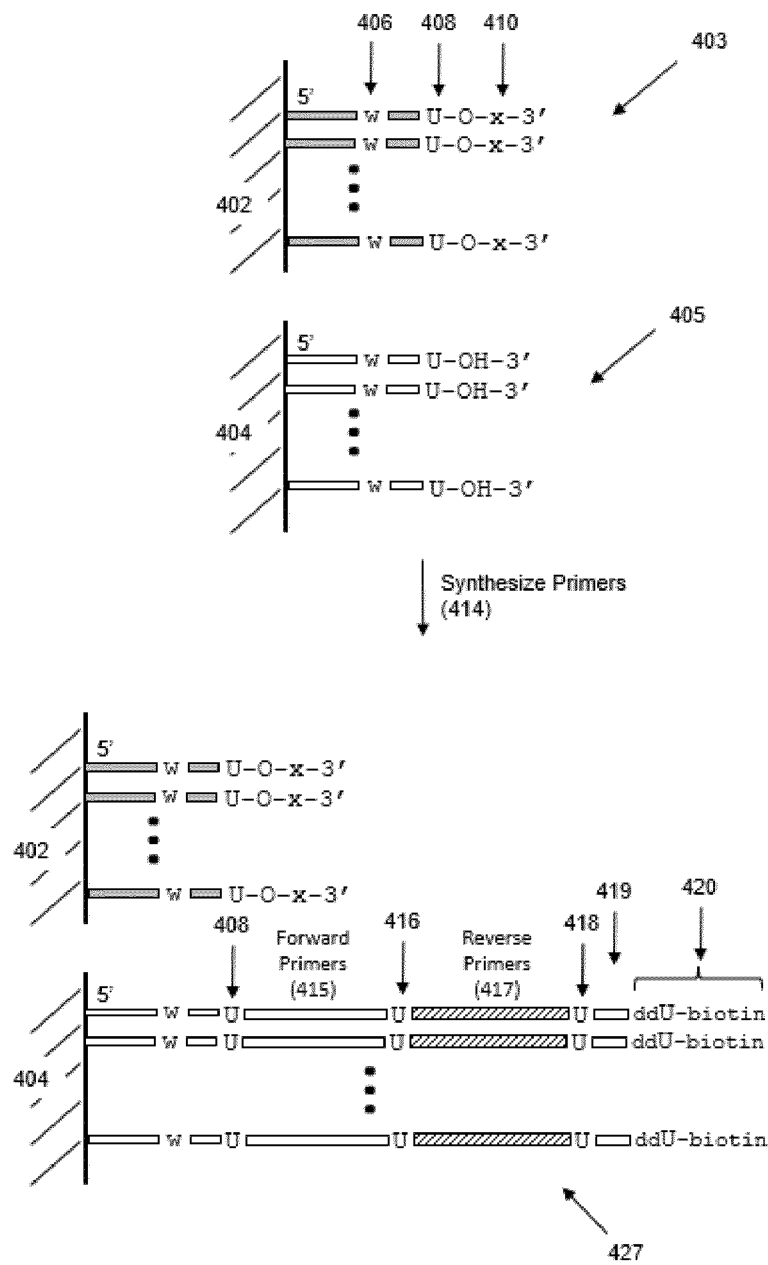
FIGS. 4A-4E illustrate the steps of embodiments for performing quantitative PCR with a Taqman probe.
Figure 4B:
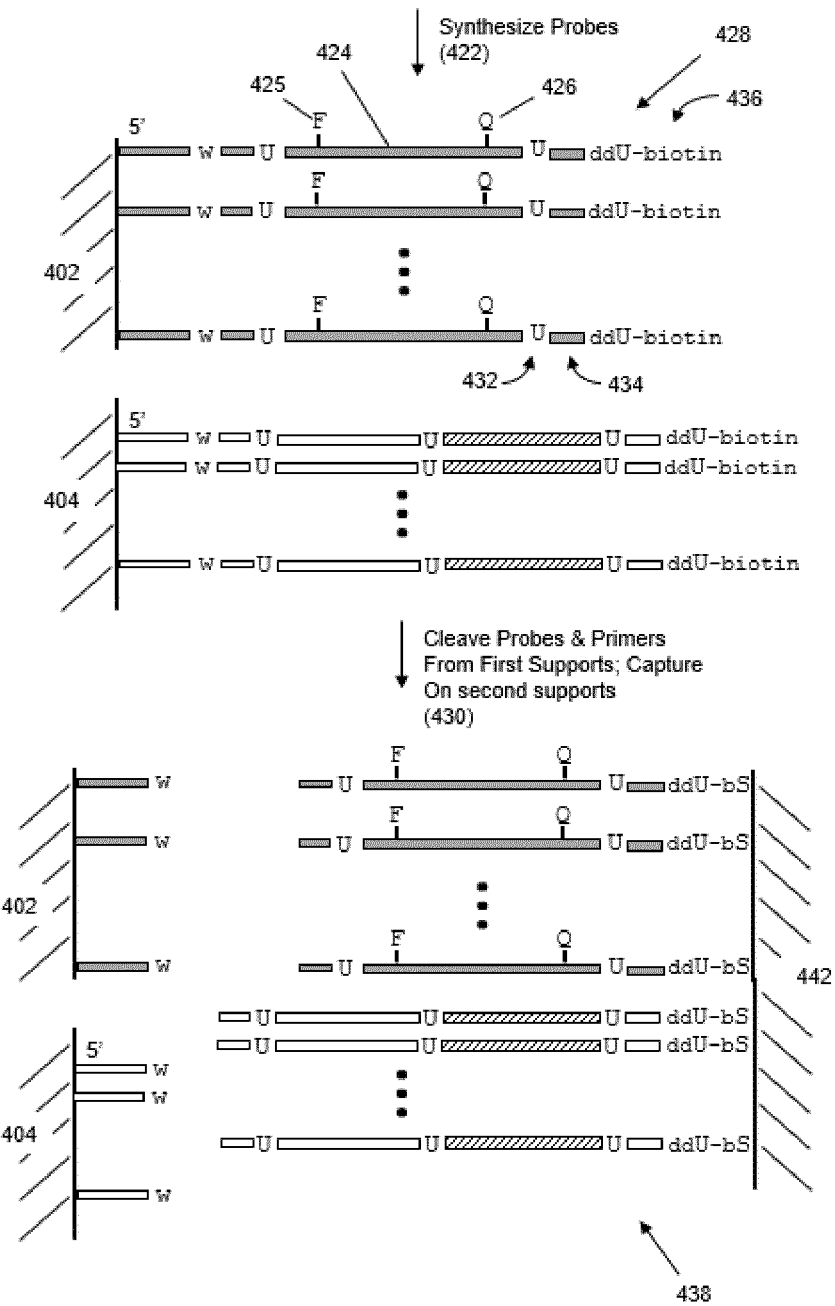
Figure 4C:
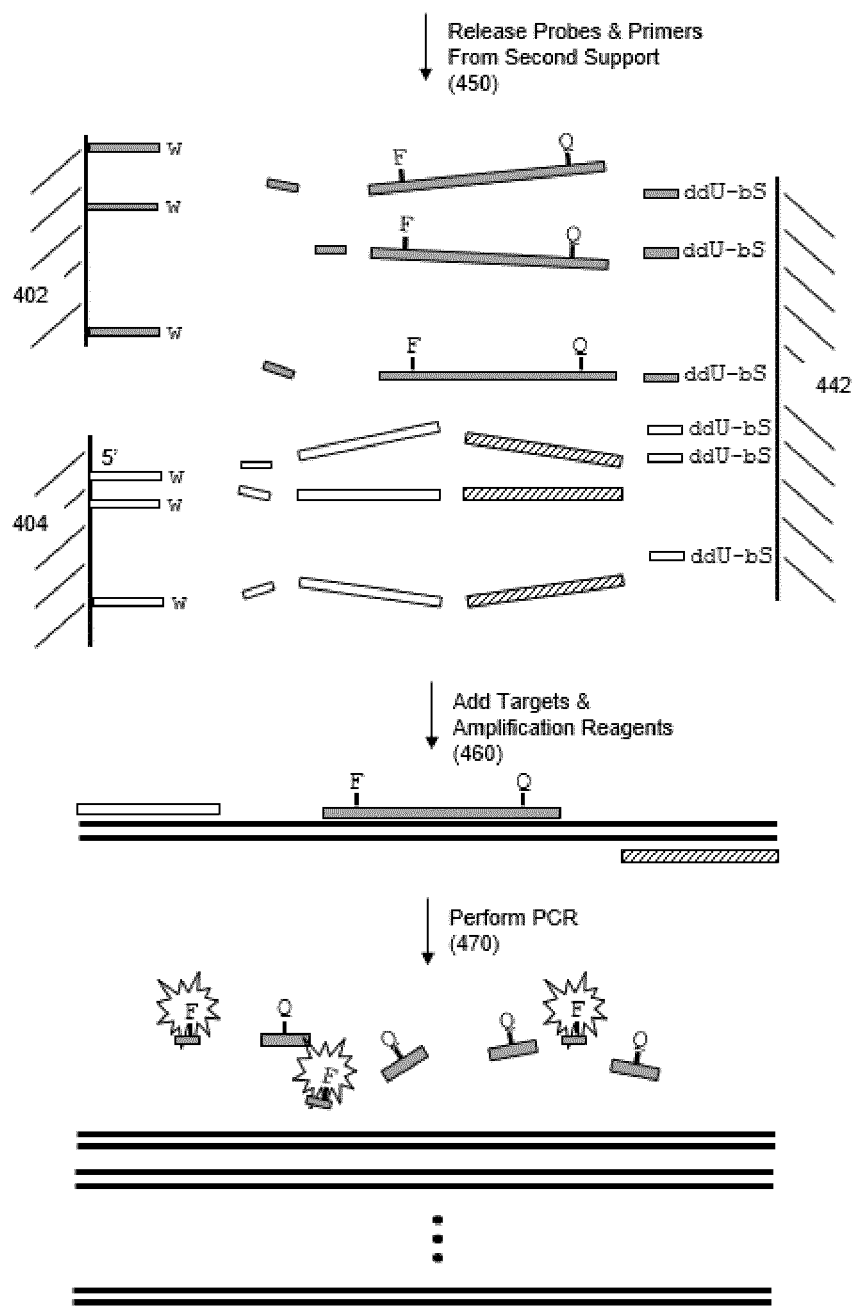

Primers and probe are synthesized and a quantative PCR implemented that follows the protocol described in Holland et al, Proc. Natl. Acad. Sci., 88: 7276-7280 (1991), for amplifying a 350 bp fragment of single stranded phage M13mp10, with some modifications. Steps of the method are illustrated in FIGS. 4A-4C. In the same reaction well are disposed first synthesis support (402) and second synthesis support (404) each comprising a magnetic agarose resin, wherein first support (402) has attached a first initiator oligonucleotide (403) with a terminal deoxyuridine (408) with a free 3'-hydroxyl and 5'-phosphorothioate linkage (406) between the $4^{th}$ and $5^{th}$ nucleotide from terminal deoxyurindine (408). Second support (404) has attached second initiator oligonucleotide (405) with terminal deoxyuridine (408) with 3'-O-azidomethyl blocking group (410) at its terminus and 5'-phosphorothioate linkage (406) between the $4^{th}$ and $5^{th}$ nucleotide from terminal deoxyuridine (408). Both initiators (403 and 405) are covalently attached by their 5'-ends to solid supports (402 and 404, respectively) using conventional linking chemistries. On second support (404) is synthesized (414) second polynucleotide (427) comprising in series (from proximal to distal direction from the solid support) (i) forward primer BW36 (28-mer, location 5241-5268 on phage M13mp1O)(415) and (ii) reverse primer BW42 (30-mer, location 5591-6662 on phage M13mp1O) (disclosed in Holland et al, cited above)(417), wherein the primers are separated by deoxyuridine (416). Immediately 3' of BW42 is deoxyuridine (419), a segment of five deoxythymidines (419) and finally biotinylated ddU (420). Such synthesis is carried out using 3'-O-aminodNTPs prepared and used as disclosed in Benner, U.S. Pat. No. 7,544,794 and Benner et al, U.S. Pat. Nos. 8,034,923 and 8,212,020. After synthesis of the primers is completed, on first support (402) is synthesized (422) first polynucleotide (428) comprising probe BW31 (30-mer) (424), wherein the 5'-terminal cytosine of BW31 is labeled with FAM (425) (FAM-labeled 3'-O-azidomethyl-dCTP being made as disclosed by Liu et al, U.S. Pat. No. 7,795,454 which is incorporated herein by reference) and the 3'-terminal C of BW31 is labeled with TAMRA (426) (TAMRA-labeled 3'-O-azidomethyl-dCTP being made as disclosed by Liu et al (cited above)). Otherwise, unlabeled 3'-O-azidomethyl-dNTPs are used in the synthesis, which are available commercially (Jena) or may be prepared as described in Liu et al (cited above). As with second polynucleotide (427), immediately 3' of BW31 is deoxyuridine (432), segment (434) of five deoxythymidines and finally biotinylated ddU (436). Amounts of the first and second solid supports are selected so that the cleaved probe will have a concentration of 0.04-0.4 µM in a 50 µL reaction volume and primers will be present at approximately twice the probe concentration. Synthesis reactions proceed by cycles of de-blocking, washing, TdT-based incorporating nucleoside triphosphates and washing, wherein reagent addition and removal steps are implemented using conventional fluid delivery and aspiration system in coordination with magnetic immobilization of the magnetic supports. When synthesis of first polynucleotide (428) is completed, both first and second polynucleotides (428 and 427) are cleaved from first support (402) and second support (404) by treating phosphorothioate linkage (406) with a silver nitrate solution as disclosed by Mag et al, Nucleic Acids Research, 19(7): 1437-1441 (1991), and Monforte et al, U.S. Pat. No. 5,830,655, which is incorporated herein by reference. After such cleavage, third support (442) (for example, magnetic agarose beads) coated with streptavidin is added to the reaction mixture so that released first and second polynucleotides (438) are captured. Captured polynucleotides (438) may be washed with magnetic supports (442, 402 and 404) held in the reaction vessel with the application of a magnetic field, after which probes (424) and forward (415) and reverse (417) primers are released (450) by cleaving the polynucleotides at deoxyurindine sites (408, 416, 418 and 432) using a conventional uracil deoxyglycosylase reaction followed by endonuclease VIII and treatment with a 3'-phosphatase. After heat inactivation of the cleavage enzymes, targets and amplification reagents are added (460) and a conventional quantitative PCR using Taq polymerase is performed (470) which releases FAM molecules (425) from probes (424)

Figure 4D:
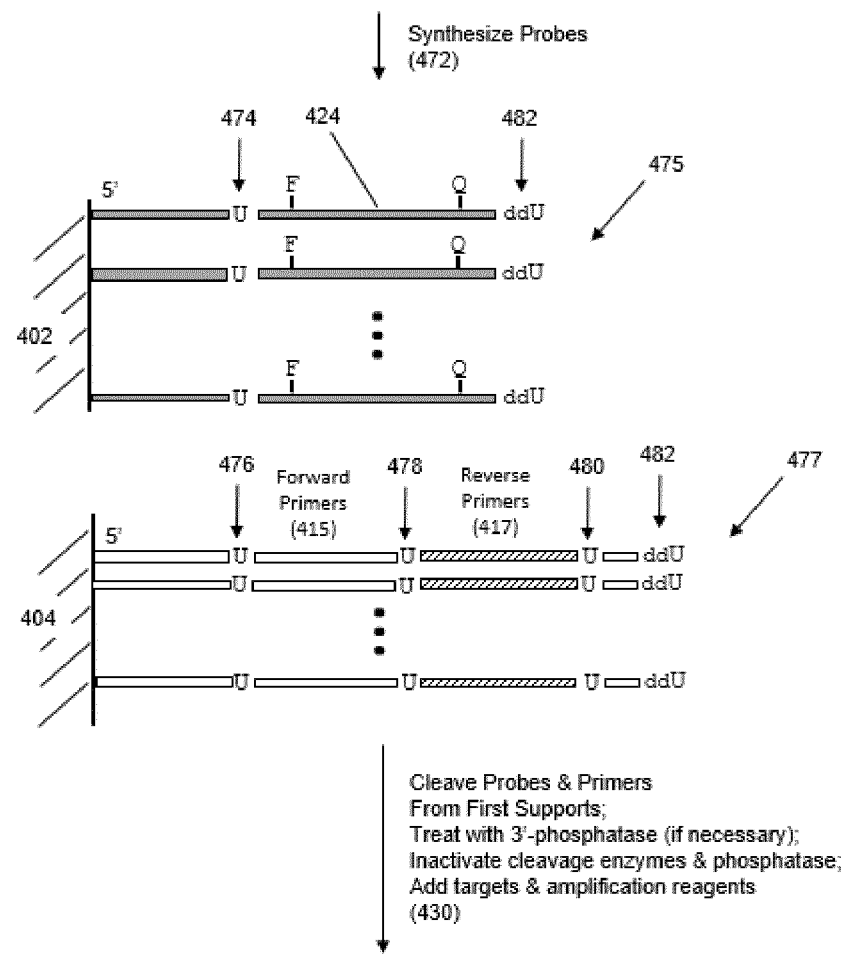

An alternative embodiment employing only first supports (402 and 404) is illustrated in FIG. 4D. Instead of using second support (442) to capture completed polynucleotides (427 and 428) (for example, to facilitate removal of used reagents), in the embodiment of FIG. 4D, second polynucleotides (427) are capped to prevent erroneous extension during the synthesis of first polynucleotide (428), intra-initiator cleavable linkage "W" (406) is eliminated; and capture moieties on the terminal nucleotides of both first and second polynucleotides are eliminated. Capping moieties (482) on probe polynucleotides (475) are attached to prevent spurious extension of probe sequences during amplification. After synthesis is completed (472), synthesis reagents may be removed or inactivated while first and second polynucleotides (475 and 477) remain attached to supports (402 and 404), after which the desired forward (415) and reverse primers (417) and probe (424) may be released in a single cleavage reaction. In this example, the single cleavage reaction cleaves first and second polynucleotides (475 and 477) at deoxyuridines (474, 476, 478 and 480) with conventional UDG/endonuclease VIII treatment to release the primers and probes. The released primers are treated with a 3'-phosphatase to generate free extendable 3'-hydroxyls, after which the cleavage enzymes and phosphatase may be inactivate, e.g. by heat inactivation, and targets and amplification reagents added to perform a qPCR.

Example 2: Serial Synthesis of Primers and Taqman Probe for qPCR

Figure 4E:
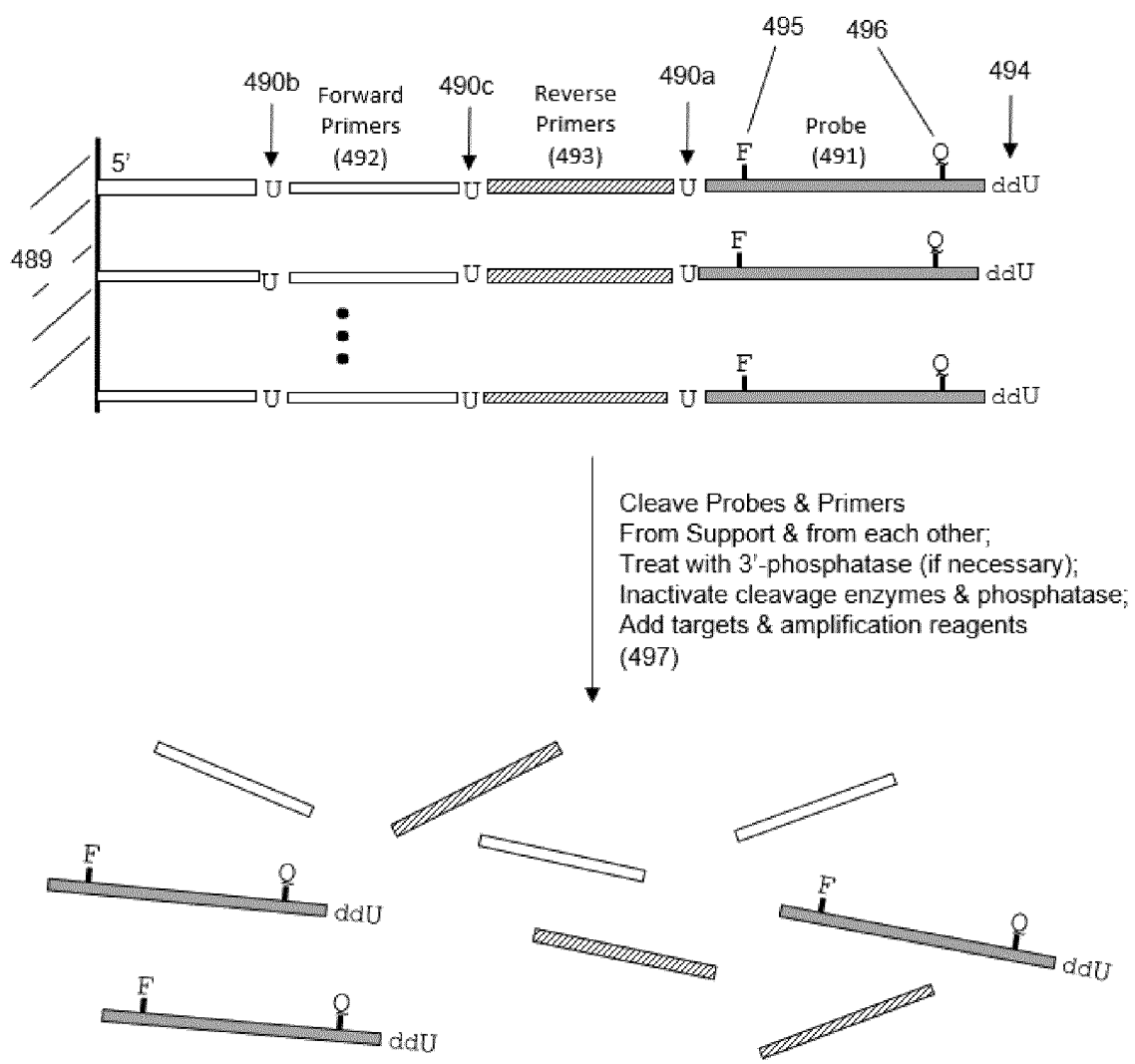

In this example, primers and probe similar to those of FIG. 4D are synthesized serially on a single support (489 of FIG. 4E). As above, initiators (488) are provided with a terminal dU (491*a*) to permit cleavage of probe (491) and primers (492 and 493) from support (489). Alternatively a photocleavable linkage may be provided in place of dU that leaves a free 3'-hydroxyl after cleavage (e.g. Urdea et al, U.S. Pat. No. 5,367,066, which is incorporated herein by reference). Further cleavable nucleotides (e.g. dU as shown, 490*c* and 490*a*) or cleavable linkages separate forward primers (492), reverse primers (493) and probes (491). Stands are synthesized as described above with the 3' ends of probe (491) being terminated with a capping agent, such as a dideoxyU moiety to prevent spurious extensions when used in a PCR. Fluorescent reporter (495) and quencher (496) may be added directly or indirectly as described above. After synthesis is completed (497), synthesis reagents may be removed or inactivated and primers and probes released with conventional UDG/endonuclease VIII treatment. The released primers are treated with a 3'-phosphatase to generate free extendable 3'-hydroxyls, after which the cleavage enzymes and phosphatase may be inactivate, e.g. by heat inactivation, and targets and amplification reagents added to perform a qPCR Definitions Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

"Amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. "Amplicon" means the product of a polynucleotide amplification reaction; that is, a clonal population of polynucleotides, which may be single stranded or double stranded, which are replicated from one or more starting sequences. "Amplifying" means producing an amplicon by carrying out an amplification reaction. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Capture moiety" is typically one member of a specific binding pair. "Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold. Typically, the affinity or avidity of a specific binding reaction is least about $10^7$ $M^{-1}$, using at least $10^8$ $M^{-1}$ to at least about $10^9$ $M^{-1}$, and often greater, including affinities or avidities up to $10^{10}$ $M^{-1}$ to $10^{-1}$ $M^{-1}$. The phrase "specific binding pair" refers to pairs of molecules, typically pairs of biomolecules, that exhibit specific binding. A wide range of specific binding pair members that can be used for capture of oligonucleotides are known in the art. Among these are small capture moieties colloquially termed "haptens" irrespective of their antigenicity. Such haptens include biotin, digoxigenin, and dinitrophenyl. Biotin can be captured using avidin, streptavidin, captavidin, neutravidin, or anti-biotin antibodies. Digoxigenin and dinitrophenyl can be captured using antibodies specific for the respective hapten.

"Functionally equivalent" in reference to amino acid positions in two or more different TdTs means (i) the amino acids at the respective positions play the same functional role in an activity of the TdTs, and (ii) the amino acids occur at homologous amino acid positions in the amino acid sequences of the respective TdTs. It is possible to identify positionally equivalent or homologous amino acid residues in the amino acid sequences of two or more different TdTs on the basis of sequence alignment and/or molecular modelling. In some embodiments, functionally equivalent amino acid positions belong to sequence motifs that are conserved among the amino acid sequences of TdTs of evolutionarily related species, e.g. genus, families, or the like. Examples of such conserved sequence motifs are described in Motea et al, Biochim. Biophys. Acta. 1804(5): 1151-1166 (2010); Delarue et al, EMBO J., 21: 427-439 (2002); and like references.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., fluorescent labels, such as mutually quenching fluorescent labels, fluorescent label linking agents, enzymes, quenching agents, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels and/or quenching agents.

"Microfluidics" device or "nanofluidics" device, used interchangeably herein, each means an integrated system for capturing, moving, mixing, dispensing or analyzing small volumes of fluid, including samples (which, in turn, may contain or comprise cellular or molecular analytes of interest), reagents, dilutants, buffers, or the like. Generally, reference to "microfluidics" and "nanofluidics" denotes different scales in the size of devices and volumes of fluids handled. In some embodiments, features of a microfluidic device have cross-sectional dimensions of less than a few hundred square micrometers and have passages, or channels, with capillary dimensions, e.g. having maximal cross-sectional dimensions of from about 500 µm to about 0.1 µm. In some embodiments, microfluidics devices have volume capacities in the range of from 1 µL to a few nL, e.g. 10-100 nL. Dimensions of corresponding features, or structures, in nanofluidics devices are typically from 1 to 3 orders of magnitude less than those for microfluidics devices. One skilled in the art would know from the circumstances of a particular application which dimensionality would be pertinent. In some embodiments, microfluidic or nanofluidic devices have one or more chambers, ports, and channels that are interconnected and in fluid communication and that are designed for carrying out one or more analytical reactions or processes, either alone or in cooperation with an appliance or instrument that provides support functions, such as sample introduction, fluid and/or reagent driving means, such as positive or negative pressure, acoustical energy, or the like, temperature control, detection systems, data collection and/or integration systems, and the like. In some embodiments, microfluidics and nanofluidics devices may further include valves, pumps, filters and specialized functional coatings on interior walls, e.g. to prevent adsorption of sample components or reactants, facilitate reagent movement by electroosmosis, or the like. Such devices may be fabricated as an integrated device in a solid substrate, which may be glass, plastic, or other solid polymeric materials, and may have a planar format for ease of detecting and monitoring sample and reagent movement, especially via optical or electrochemical methods. In some embodiments, such devices are disposable after a single use. In some embodiments, microfluidic and nanofluidic devices include devices that form and control the movement, mixing, dispensing and analysis of droplets, such as, aqueous droplets immersed in an immiscible fluid, such as a light oil. The fabrication and operation of microfluidics and nanofluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No.

6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437; Cao, "Nanostructures & Nanomaterials: Synthesis, Properties & Applications," (Imperial College Press, London, 2004); Haeberle et al, LabChip, 7: 1094-1110 (2007); Cheng et al, Biochip Technology (CRC Press, 2001); and the like.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Nucleic acid sequence-based amplification" or "NASBA" is an amplification reaction based on the simultaneous activity of a reverse transcriptase (usually avian myeloblastosis virus (AMV) reverse transcriptase), an RNase H, and an RNA polymerase (usually T7 RNA polymerase) that uses two oligonucleotide primers, and which under conventional conditions can amplify a target sequence by a factor in the range of $10^9$ to $10^{12}$ in 90 to 120 minutes. In a NASBA reaction, nucleic acids are a template for the amplification reaction only if they are single stranded and contain a primer binding site. Because NASBA is isothermal (usually carried out at 41° C. with the above enzymes), specific amplification of single stranded RNA may be accomplished if denaturation of double stranded DNA is prevented in the sample preparation procedure. That is, it is possible to detect a single stranded RNA target in a double stranded DNA background without getting false positive results caused by complex genomic DNA, in contrast with other techniques, such as RT-PCR. By using fluorescent indicators compatible with the reaction, such as molecular beacons, NASBAs may be carried out with real-time detection of the amplicon. Molecular beacons are stem-and-loop-structured oligonucleotides with a fluorescent label at one end and a quencher at the other end, e.g. 5'-fluorescein and 3'-(4-(dimethylamino)phenyl)azo) benzoic acid (i.e., 3'-DABCYL), as disclosed by Tyagi and Kramer (cited above). An exemplary molecular beacon may have complementary stem strands of six nucleotides, e.g. 4 G's or C's and 2 A's or T's, and a target-specific loop of about 20 nucleotides, so that the molecular beacon can form a stable hybrid with a target sequence at reaction temperature, e.g. 41° C. A typical NASBA reaction mix is 80 mM Tris-HCl [pH 8.5], 24 mM $MgCl_2$, 140 mM KCl, 1.0 mM DTT, 2.0 mM of each dNTP, 4.0 mM each of ATP, UTP and CTP, 3.0 mM GTP, and 1.0 mM ITP in 30% DMSO. Primer concentration is 0.1 µM and molecular beacon concentration is 40 nM. Enzyme mix is 375 sorbitol, 2.1 µg BSA, 0.08 U RNase H, 32 U T7 RNA polymerase, and 6.4 U AMV reverse transcriptase. A reaction may comprise 5 µL sample, 10 µL NASBA reaction mix, and 5 µL enzyme mix, for a total reaction volume of 20 µL. Further guidance for carrying out real-time NASBA reactions is disclosed in the following references that are incorporated by reference: Polstra et al, BMC Infectious Diseases, 2: 18 (2002); Leone et al, Nucleic Acids Research, 26: 2150-2155 (1998); Gulliksen et al, Anal. Chem., 76: 9-14 (2004); Weusten et al, Nucleic Acids Research, 30(6) e26 (2002); Deiman et al, Mol. Biotechnol., 20: 163-179 (2002). Nested NASBA reactions are carried out similarly to nested PCRs; namely, the amplicon of a first NASBA reaction becomes the sample for a second NASBA reaction using a new set of primers, at least one of which binds to an interior location of the first amplicon.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. In some embodiments, a 10-100 µL reaction volume is employed; in some embodiments, a 20-50 µL reaction volume is employed. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("tagman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 10, or from 2 to 6, or more typically, from 2 to 4. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. RNA template is given to the reaction mixture, the first primer, with the T7 promoter region on its 5' end, attaches to its complementary site at the 3' end of the template. In RT-PCR, reverse transcriptase synthesizes the opposite, complementary DNA strand ("first DNA strand"), extending the 3' end of the primer, moving upstream along the RNA template. RNAse H destroys the RNA template from the DNA-RNA compound (RNAse H only destroys RNA in RNA-DNA hybrids, but not single-stranded RNA). The second primer attaches to the 5' end of the (antisense) DNA strand. Reverse transcriptase again synthesizes another DNA strand ("second DNA strand") from the attached primer resulting in double stranded DNA. T7 RNA polymerase binds to the promoter region on the double strand. Since T7 RNA polymerase can only transcribe in the 3' to 5' direction the sense DNA is transcribed and an anti-sense RNA is produced. This is repeated, and the polymerase continuously produces complementary RNA strands of this template which results in amplification. Now a cyclic phase can begin similar to the previous steps. Here, however, the second primer first binds to the (−)RNA. The reverse transcriptase now produces a (+)cDNA/(−)RNA duplex. RNAse H again degrades the RNA and the first primer, the one with the T7 promoter region, binds to the now single stranded+ (cDNA). The reverse transcriptase now produces the complementary (−)DNA, creating a dsDNA duplex. Exactly like step 6 (above), the T7 polymerase binds to the promoter region, produces RNA, and the cycle is complete.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999), or like reference. Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms' usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)) Alignment for purposes of determining percent amino acid sequence identity can be achieved in various ways that are within the skill in the art, for instance, using publicly available computer software available on internet web sites. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Sequence tag" (or "tag") or "barcode" means an oligonucleotide that is attached to a polynucleotide or template molecule and is used to identify and/or track the polynucleotide or template in a reaction or a series of reactions. A sequence tag may be attached to the 3'- or 5'-end of a polynucleotide or template or it may be inserted into the interior of such polynucleotide or template to form a linear conjugate, sometime referred to herein as a "tagged polynucleotide," or "tagged template," or "tag-polynucleotide conjugate," "tag-molecule conjugate," or the like. Sequence tags may vary widely in size and compositions; the following references, which are incorporated herein by reference, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g. via a hybridization reaction or via an enzymatic reaction, such as sequencing; whether they are labeled, e.g. with a fluorescent dye or the like; the number of distinguishable oligonucleotide tags required to unambiguously identify a set of polynucleotides, and the like, and how different must tags of a set be in order to ensure reliable identification, e.g. freedom from cross hybridization or misidentification from sequencing errors. In one aspect, sequence tags can each have a length within a range of from 2 to 36 nucleotides, or from 4 to 30 nucleotides, or from 8 to 20 nucleotides, or from 6 to 10 nucleotides, respectively. In one aspect, sets of sequence tags are used wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr). In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

The invention claimed is:

1. A method of synthesizing a plurality of oligonucleotides and performing oligonucleotide-based assays in a single reaction vessel, the method comprising the steps of:
   a) repeating in a reaction vessel cycles of (i) contacting under elongation conditions an initiator having a free 3'-hydroxyl or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until elongated fragments are formed each containing a plurality of oligonucleotides separated from one another and from the initiator by cleavable nucleotides;
   b) cleaving the cleavable nucleotides to free at least one of the plurality of oligonucleotides;
   c) adding reagents for the oligonucleotide-based assay; and
   d) performing the oligonucleotide-based assay.

2. The method of claim 1 wherein said oligonucleotide-based assay is a polymerase chain reaction (PCR) and wherein said step of adding further includes adding a polymerase, polymerase reaction buffer, nucleoside triphosphates, and one or more target polynucleotides at least one of which has complementary segments to at least two of said oligonucleotides so that sequences between the complementary segments are amplified in a PCR.

3. The method of claim 1, wherein said step of cleaving comprises the application of an enzymatic activity and wherein after cleavage the enzymatic activity is deactivated.

4. The method of claim 1 wherein said oligonucleotide-based assay is a nucleic acid sequence-based amplification (NASBA) and wherein said step c) further includes adding an RNA polymerase, an RNAse H, a reverse transcriptase, NASBA reaction buffer, nucleoside triphosphates, and one or more single stranded target nucleic acids at least one of which has complementary segment to at least one of said oligonucleotides so that sequences between the complementary segments are amplified in a NASBA reaction.

5. A method of synthesizing a plurality of oligonucleotides and performing oligonucleotide-based assays in a single reaction vessel, the method comprising the steps of:
   a) repeating in a reaction vessel cycles of (i) contacting under elongation conditions an initiator having a free 3'-hydroxyl or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until elongated fragments are formed each containing a plurality of oligonucleotides separated from one another and from the initiator by cleavable nucleotides;
   b) cleaving the cleavable nucleotides to free at least one of the plurality of oligonucleotides;
   c) adding reagents for the oligonucleotide-based assay; and
   d) performing the oligonucleotide-based assay, wherein said initiators and said elongation fragments are attached to a support and wherein said step of cleaving leaves one of said oligonucleotides of said plurality attached to the support.

6. A method of synthesizing a plurality of oligonucleotides in a single reaction vessel, the method comprising the steps of:
   a) providing one or more supports with two or more populations of initiators wherein the initiators of each population are terminated by a cleavable linkage or cleavable nucleotide having a population-specific 3'-O-blocking group removable by deblocking conditions orthogonal to the deblocking conditions of the 3'-O-blocking groups of every other population of initiators;
   b) deblocking population-specific blocking groups of a population of initiators or elongated fragments to form initiators or elongated fragments having free 3'-hydroxyls;
   c) contacting under elongation conditions the population of initiators or its elongated fragments having free 3'-hydroxyls with a 3'-O-blocked nucleoside triphosphate and a template-independent DNA polymerase so that the initiators or elongated fragments are elongated by incorporation of the 3'-O-blocked nucleoside triphosphate to form 3'-O-blocked elongated fragments;
   d) repeating steps b) and c) for each population of initiators until elongated fragments are formed having nucleotide sequences of the plurality of oligonucleotides.

7. The method of 6 further including the steps of e) deblocking said elongated fragments, and f) cleaving said cleavable linkages or cleavable nucleotides to free said elongated fragments.

8. The method of claim 7 further including the steps of g) adding reagents for an oligonucleotide-based assay, and h) performing said oligonucleotide-based assay.

9. The method of claim 6, wherein said steps b) through d) are implemented for each of said populations of initiators consecutively so that each of said oligonucleotides of said plurality are synthesized consecutively.

10. The method of claim 6, wherein said steps b) through d) are implemented for each of said populations of initiators alternatively so that each of said oligonucleotides of said plurality are synthesized in parallel.

11. The method of claim 6, wherein said support is a solid support.

12. A method of synthesizing a plurality of oligonucleotides and performing oligonucleotide-based assays in a single reaction vessel, the method comprising the steps of:
   a) repeating in a reaction vessel cycles of (i) contacting under elongation conditions an initiator having a free 3'-hydroxyl or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until elongated fragments are formed each containing a plurality of oligonucleotides separated from one another and from the initiator by cleavable nucleotides;
   b) cleaving the cleavable nucleotides to free at least one of the plurality of oligonucleotides;
   c) adding reagents for the oligonucleotide-based assay; and
   d) performing the oligonucleotide-based assay, wherein said template-independent DNA polymerase is a terminal deoxynucleotidyl transferase (TdT).

13. The method of claim 12, wherein said TdT is a TdT variant having an amino acid sequence with at least 90 percent identity to one of SEQ ID NO: 2, 3, 4, 5, 6, 7, 8, 9, 10, 11, 12, 13, 14 or 15 with a substitution of methionine at position 63 with respect to SEQ ID NOs: 2, 3, 4, 6, 7, 12 and 14; or methionine at position 73 with respect to SEQ ID NO: 9; or methionine at position 64 with respect to SEQ ID NO: 10; or methionine at position 61 with respect to SEQ ID NO: 11; or methionine at position 66 with respect to SEQ ID NO: 15; and a substitution of a first arginine at position 207 with respect to SEQ ID NOs: 2, 3, 4, 6, 7, 9, 12 and 13; or a first arginine at position 206 with respect to SEQ ID NO: 5; or a first arginine at position 208 with respect to SEQ ID NOs: 8 or 10; or a first arginine at position 205 with respect to SEQ ID NO: 11; or a first arginine at position 216 with respect to SEQ ID NO: 14; or a first arginine at position 210 with respect to SEQ ID NO: 15.

14. The method of claim 13, wherein said TdT variant further has one or more of the following substitutions: a cysteine at position 173 with respect to SEQ ID NOs: 2, 3, 4, 6, 7, 9, 12 and 13; or cysteine at position 172 with respect to SEQ ID NO: 5; or cysteine at position 174 with respect to SEQ ID NOs: 8 and 10; or cysteine at position 171 with respect to SEQ ID NO: 11; or cysteine at position 176 with respect to SEQ ID NO: 15; or cysteine at position 182 with respect to SEQ ID NO: 14; or a second arginine at position 325 with respect to SEQ ID NO: 2, 9 and 13; or a second arginine at position 324 with respect to SEQ ID NOs 3 and 4; or a second arginine at position 320 with respect to SEQ ID NO: 5; or a second arginine at position 331 with respect to SEQ ID NOs: 6 and 8; or a second arginine at position 323 with respect to SEQ ID NO: 11; or a second arginine at position 328 with respect to SEQ ID NOs: 12 and 15; or a second arginine at position 338 with respect to SEQ ID NO: 14: or a glutamic acid at position 328 with respect to SEQ ID NOs: 2, 7, 9 and 13; or glutamic acid at position 327 with respect to SEQ ID NOs: 3 and 4; or glutamic acid at position 334 with respect to SEQ ID NOs: 6 and 8; or glutamic acid at position 329 with respect to SEQ ID NO: 10; or glutamic acid at position 326 with respect to SEQ ID NO: 11; or glutamic acid at position 331 with respect to SEQ ID NOs: 12 and 15.

15. The method of claim 14, wherein said substitution of said methionine is R or Q; said substitution of said cysteine is G or R; said substitution of said first arginine is L or N; said substitution of said second arginine is P, N, A or V; and said substitution of said glutamic acid is N, L, T, S or K.

16. A method for synthesizing a plurality of oligonucleotides in a single reaction vessel, the method comprising the steps of:
(a) providing a plurality of different initiators attached to one or more supports, wherein at least one initiator of the plurality has free 3'-hydroxyls and wherein at least one initiator of the plurality has 3'-O-blocked terminal nucleotides;
(b) synthesizing the plurality of oligonucleotides by repeated cycles of template-free enzymatic nucleotide additions to each different initiator or its extension products of 3'-O-blocked nucleoside triphosphates, wherein the 3'-O-blocked nucleoside triphosphate has a blocking group that is removable under deblocking conditions orthogonal to deblocking conditions for removing blocking groups of other initiators of the plurality, and wherein each of the repeated cycles comprises a deblocking step under said deblocking conditions; and
(c) releasing oligonucleotides from the extension products and the one or more solid supports.

17. The method of claim 16, wherein said plurality of oligonucleotides is equal to or greater than said plurality of different initiators.

18. The method of claim 16, further including the steps of (d) adding reagents for an oligonucleotide-based assay and (e) performing the oligonucleotide-based assay.

* * * * *

SEQUENCE LISTING

<160> NUMBER OF SEQ ID NOS: 15

<210> SEQ ID NO 1

<211> LENGTH: 510
<212> TYPE: PRT
<213> ORGANISM: ARTIFICIAL SEQUENCE
<220> FEATURE:
<223> OTHER INFORMATION: TdT

<400> SEQUENCE: 1

```
Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380
```

```
Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
        420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
        450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
                485                 490                 495

His Leu Gly Leu Asp Tyr Ile Glu Pro Trp Glu Arg Asn Ala
            500                 505                 510

<210> SEQ ID NO 2
<211> LENGTH: 381
<212> TYPE: PRT
<213> ORGANISM: ARTIFICIAL SEQUENCE
<220> FEATURE:
<223> OTHER INFORMATION: TRUNCATED TdT

<400> SEQUENCE: 2

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240
```

```
Lys Gln Gln Gly Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
                260                 265                 270

Gln Lys Cys Phe Leu Ile Leu Lys Leu Asp His Gly Arg Val His Ser
                275                 280                 285

Glu Lys Ser Gly Gln Gln Glu Gly Lys Gly Trp Lys Ala Ile Arg Val
            290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Arg Thr
                340                 345                 350

Lys Arg Val Phe Leu Glu Ala Glu Ser Glu Glu Glu Ile Phe Ala His
                355                 360                 365

Leu Gly Leu Asp Tyr Ile Glu Pro Trp Glu Arg Asn Ala
                370                 375                 380

<210> SEQ ID NO 3
<211> LENGTH: 380
<212> TYPE: PRT
<213> ORGANISM: ARTIFICIAL SEQUENCE
<220> FEATURE:
<223> OTHER INFORMATION: BOVINE TRUNCATED TdT

<400> SEQUENCE: 3

Asp Tyr Ser Ala Thr Pro Asn Pro Gly Phe Gln Lys Thr Pro Pro Leu
1               5                   10                  15

Ala Val Lys Lys Ile Ser Gln Tyr Ala Cys Gln Arg Lys Thr Thr Leu
                20                  25                  30

Asn Asn Tyr Asn His Ile Phe Thr Asp Ala Phe Glu Ile Leu Ala Glu
            35                  40                  45

Asn Ser Glu Phe Lys Glu Asn Glu Val Ser Tyr Val Thr Phe Met Arg
50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Ser
    130                 135                 140

Leu Ser Lys Ile Met Ser Asp Lys Thr Leu Lys Phe Thr Lys Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Ile Gly His Asp Val Asp Phe Leu Ile Thr Ser Pro Gly Ser
    210                 215                 220
```

```
Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Ser Thr Phe Glu
            245                 250                 255

Lys Phe Lys Leu Pro Ser Arg Gln Val Asp Thr Leu Asp His Phe Gln
            260                 265                 270

Lys Cys Phe Leu Ile Leu Lys Leu His His Gln Arg Val Asp Ser Ser
            275                 280                 285

Lys Ser Asn Gln Gln Glu Gly Lys Thr Trp Lys Ala Ile Arg Val Asp
            290                 295                 300

Leu Val Met Cys Pro Tyr Glu Asn Arg Ala Phe Ala Leu Leu Gly Trp
305                 310                 315                 320

Thr Gly Ser Arg Gln Phe Glu Arg Asp Ile Arg Arg Tyr Ala Thr His
            325                 330                 335

Glu Arg Lys Met Met Leu Asp Asn His Ala Leu Tyr Asp Lys Thr Lys
            340                 345                 350

Arg Val Phe Leu Lys Ala Glu Ser Glu Glu Ile Phe Ala His Leu
            355                 360                 365

Gly Leu Asp Tyr Ile Glu Pro Trp Glu Arg Asn Ala
            370                 375                 380

<210> SEQ ID NO 4
<211> LENGTH: 380
<212> TYPE: PRT
<213> ORGANISM: ARTIFICIAL SEQUENCE
<220> FEATURE:
<223> OTHER INFORMATION: HUMAN TRUNCATED TdT

<400> SEQUENCE: 4

Asp Tyr Ser Asp Ser Thr Asn Pro Gly Pro Pro Lys Thr Pro Pro Ile
1               5                   10                  15

Ala Val Gln Lys Ile Ser Gln Tyr Ala Cys Gln Arg Arg Thr Thr Leu
            20                  25                  30

Asn Asn Cys Asn Gln Ile Phe Thr Asp Ala Phe Asp Ile Leu Ala Glu
        35                  40                  45

Asn Cys Glu Phe Arg Glu Asn Glu Asp Ser Cys Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Lys Val Arg Ser Asp Lys Ser Leu Lys Phe Thr Arg Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Ser Val Leu Val Lys Glu Ala Val Trp Ala
            180                 185                 190

Phe Leu Pro Asp Ala Phe Val Thr Met Thr Gly Gly Phe Arg Arg Gly
        195                 200                 205
```

-continued

```
Lys Lys Met Gly His Asp Val Asp Phe Leu Ile Thr Ser Pro Gly Ser
            210                 215                 220

Thr Glu Asp Glu Glu Gln Leu Leu Gln Lys Val Met Asn Leu Trp Glu
225                 230                 235                 240

Lys Lys Gly Leu Leu Leu Tyr Tyr Asp Leu Val Glu Ser Thr Phe Glu
                245                 250                 255

Lys Leu Arg Leu Pro Ser Arg Lys Val Asp Ala Leu Asp His Phe Gln
            260                 265                 270

Lys Cys Phe Leu Ile Phe Lys Leu Pro Arg Gln Arg Val Asp Ser Asp
        275                 280                 285

Gln Ser Ser Trp Gln Glu Gly Lys Thr Trp Lys Ala Ile Arg Val Asp
    290                 295                 300

Leu Val Leu Cys Pro Tyr Glu Arg Arg Ala Phe Ala Leu Leu Gly Trp
305                 310                 315                 320

Thr Gly Ser Arg Gln Phe Glu Arg Asp Leu Arg Arg Tyr Ala Thr His
                325                 330                 335

Glu Arg Lys Met Ile Leu Asp Asn His Ala Leu Tyr Asp Lys Thr Lys
            340                 345                 350

Arg Ile Phe Leu Lys Ala Glu Ser Glu Glu Glu Ile Phe Ala His Leu
        355                 360                 365

Gly Leu Asp Tyr Ile Glu Pro Trp Glu Arg Asn Ala
    370                 375                 380
```

<210> SEQ ID NO 5
<211> LENGTH: 376
<212> TYPE: PRT
<213> ORGANISM: ARTIFICIAL SEQUENCE
<220> FEATURE:
<223> OTHER INFORMATION: CHICKEN TRUNCATED TdT

<400> SEQUENCE: 5

```
Gln Tyr Pro Thr Leu Lys Thr Pro Glu Ser Glu Val Ser Ser Phe Thr
1               5                   10                  15

Ala Ser Lys Val Ser Gln Tyr Ser Cys Gln Arg Lys Thr Thr Leu Asn
            20                  25                  30

Asn Cys Asn Lys Lys Phe Thr Asp Ala Phe Glu Ile Met Ala Glu Asn
        35                  40                  45

Tyr Glu Phe Lys Glu Asn Glu Ile Phe Cys Leu Glu Phe Leu Arg Ala
    50                  55                  60

Ala Ser Val Leu Lys Ser Leu Pro Phe Pro Val Thr Arg Met Lys Asp
65                  70                  75                  80

Ile Gln Gly Leu Pro Cys Met Gly Asp Arg Val Arg Asp Val Ile Glu
                85                  90                  95

Glu Ile Ile Glu Glu Gly Glu Ser Ser Arg Ala Lys Asp Val Leu Asn
            100                 105                 110

Asp Glu Arg Tyr Lys Ser Phe Lys Glu Phe Thr Ser Val Phe Gly Val
        115                 120                 125

Gly Val Lys Thr Ser Glu Lys Trp Phe Arg Met Gly Leu Arg Thr Val
    130                 135                 140

Glu Glu Val Lys Ala Asp Lys Thr Leu Lys Leu Ser Lys Met Gln Arg
145                 150                 155                 160

Ala Gly Phe Leu Tyr Tyr Glu Asp Leu Val Ser Cys Val Ser Lys Ala
                165                 170                 175

Glu Ala Asp Ala Val Ser Ser Ile Val Lys Asn Thr Val Cys Thr Phe
            180                 185                 190
```

```
Leu Pro Asp Ala Leu Val Thr Ile Thr Gly Gly Phe Arg Arg Gly Lys
        195                 200                 205

Lys Ile Gly His Asp Ile Asp Phe Leu Ile Thr Ser Pro Gly Gln Arg
        210                 215                 220

Glu Asp Asp Glu Leu Leu His Lys Gly Leu Leu Tyr Cys Asp Ile
225                 230                 235                 240

Ile Glu Ser Thr Phe Val Lys Glu Gln Ile Pro Ser Arg His Val Asp
                245                 250                 255

Ala Met Asp His Phe Gln Lys Cys Phe Ala Ile Leu Lys Leu Tyr Gln
                260                 265                 270

Pro Arg Val Asp Asn Ser Ser Tyr Asn Met Ser Lys Lys Cys Asp Met
        275                 280                 285

Ala Glu Val Lys Asp Trp Lys Ala Ile Arg Val Asp Leu Val Ile Thr
        290                 295                 300

Pro Phe Glu Gln Tyr Ala Tyr Ala Leu Leu Gly Trp Thr Gly Ser Arg
305                 310                 315                 320

Gln Phe Gly Arg Asp Leu Arg Arg Tyr Ala Thr His Glu Arg Lys Met
                325                 330                 335

Met Leu Asp Asn His Ala Leu Tyr Asp Lys Arg Lys Val Phe Leu
                340                 345                 350

Lys Ala Gly Ser Glu Glu Ile Phe Ala His Leu Gly Leu Asp Tyr
        355                 360                 365

Val Glu Pro Trp Glu Arg Asn Ala
        370                 375

<210> SEQ ID NO 6
<211> LENGTH: 387
<212> TYPE: PRT
<213> ORGANISM: ARTIFICIAL SEQUENCE
<220> FEATURE:
<223> OTHER INFORMATION: Possum truncated

<400> SEQUENCE: 6

Ser Ala Asn Pro Asp Pro Thr Ala Gly Thr Leu Asn Ile Leu Pro Pro
1               5                   10                  15

Thr Thr Lys Thr Ile Ser Gln Tyr Ala Cys Gln Arg Arg Thr Thr Ile
                20                  25                  30

Asn Asn His Asn Gln Arg Phe Thr Asp Ala Phe Glu Ile Leu Ala Lys
            35                  40                  45

Asn Tyr Glu Phe Lys Glu Asn Asp Asp Thr Cys Leu Thr Phe Met Arg
        50                  55                  60

Ala Ile Ser Val Leu Lys Cys Leu Pro Phe Glu Val Val Ser Leu Lys
65                  70                  75                  80

Asp Thr Glu Gly Leu Pro Trp Ile Gly Asp Glu Val Lys Gly Ile Met
                85                  90                  95

Glu Glu Ile Ile Glu Asp Gly Glu Ser Leu Glu Val Gln Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ala Asp Lys Trp Tyr Arg Met Gly Phe Arg Thr
    130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                165                 170                 175
```

-continued

```
Ala Glu Ala Asp Ala Val Ser Leu Leu Val Gln Asp Ala Val Trp Thr
            180                 185                 190

Phe Leu Pro Asp Ala Leu Val Thr Ile Thr Gly Gly Phe Arg Arg Gly
        195                 200                 205

Lys Glu Phe Gly His Asp Val Asp Phe Leu Ile Thr Ser Pro Gly Ala
    210                 215                 220

Glu Lys Glu Gln Glu Asp Gln Leu Leu Gln Lys Val Thr Asn Leu Trp
225                 230                 235                 240

Lys Lys Gln Gly Leu Leu Leu Tyr Cys Asp Leu Ile Glu Ser Thr Phe
                245                 250                 255

Glu Asp Leu Lys Leu Pro Ser Arg Lys Ile Asp Ala Leu Asp His Phe
            260                 265                 270

Gln Lys Cys Phe Leu Ile Leu Lys Leu Tyr His His Lys Glu Asp Lys
        275                 280                 285

Arg Lys Trp Glu Met Pro Thr Gly Ser Asn Glu Ser Glu Ala Lys Ser
    290                 295                 300

Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Lys Ala Lys Ser Glu
        355                 360                 365

Glu Glu Ile Phe Ala His Leu Gly Leu Glu Tyr Ile Gln Pro Ser Glu
    370                 375                 380

Arg Asn Ala
385
```

<210> SEQ ID NO 7
<211> LENGTH: 381
<212> TYPE: PRT
<213> ORGANISM: ARTIFICIAL SEQUENCE
<220> FEATURE:
<223> OTHER INFORMATION: New truncated shrew

<400> SEQUENCE: 7

```
Asp Cys Pro Ala Ser His Asp Ser Ser Pro Gln Lys Thr Glu Ser Ala
1               5                   10                  15

Ala Val Gln Lys Ile Ser Gln Tyr Ala Cys Gln Arg Arg Thr Thr Leu
            20                  25                  30

Asn Asn His Asn His Ile Phe Thr Asp Ala Phe Glu Ile Leu Ala Glu
        35                  40                  45

Asn Cys Glu Phe Arg Glu Asn Glu Gly Ser Tyr Val Thr Tyr Met Arg
    50                  55                  60

Ala Ala Ser Val Leu Lys Ser Leu Pro Phe Ser Ile Ile Ser Met Lys
65                  70                  75                  80

Asp Thr Glu Gly Ile Pro Cys Leu Ala Asp Lys Val Lys Cys Val Ile
                85                  90                  95

Glu Glu Ile Ile Glu Asp Gly Glu Ser Ser Val Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Leu Gly Phe Arg Thr
    130                 135                 140
```

Leu Ser Gly Ile Met Asn Asp Lys Thr Leu Lys Leu Thr His Met Gln
145                 150                 155                 160

Lys Ala Gly Phe Leu Tyr Tyr Glu Asp Leu Val Ser Cys Val Thr Arg
            165                 170                 175

Ala Glu Ala Glu Ala Val Gly Val Leu Val Lys Glu Ala Val Trp Ala
        180                 185                 190

Phe Leu Pro Asp Ala Ile Val Thr Met Thr Gly Gly Phe Arg Arg Gly
        195                 200                 205

Lys Lys Val Gly His Asp Val Asp Phe Leu Ile Thr Ser Pro Glu Ala
210                 215                 220

Thr Glu Glu Gln Glu Gln Gln Leu Leu His Lys Val Ile Thr Phe Trp
225                 230                 235                 240

Glu Lys Glu Gly Leu Leu Leu Tyr Cys Asp Leu Tyr Glu Ser Thr Phe
            245                 250                 255

Glu Lys Leu Lys Met Pro Ser Arg Lys Val Asp Ala Leu Asp His Phe
            260                 265                 270

Gln Lys Cys Phe Leu Ile Leu Lys Leu His Arg Glu Cys Val Asp Asp
        275                 280                 285

Gly Thr Ser Ser Gln Leu Gln Gly Lys Thr Trp Lys Ala Ile Arg Val
290                 295                 300

Asp Leu Val Val Cys Pro Tyr Glu Cys Arg Ala Phe Ala Leu Leu Gly
305                 310                 315                 320

Trp Thr Gly Ser Pro Gln Phe Glu Arg Asp Leu Arg Arg Tyr Ala Thr
            325                 330                 335

His Glu Arg Lys Met Met Leu Asp Asn His Ala Leu Tyr Asp Lys Thr
            340                 345                 350

Lys Arg Lys Phe Leu Ser Ala Asp Ser Glu Glu Asp Ile Phe Ala His
        355                 360                 365

Leu Gly Leu Asp Tyr Ile Glu Pro Trp Glu Arg Asn Ala
        370                 375                 380

<210> SEQ ID NO 8
<211> LENGTH: 387
<212> TYPE: PRT
<213> ORGANISM: ARTIFICIAL SEQUENCE
<220> FEATURE:
<223> OTHER INFORMATION: Python truncated

<400> SEQUENCE: 8

Glu Lys Tyr Gln Leu Pro Glu Asp Glu Asp Arg Ser Val Thr Ser Asp
1               5                   10                  15

Leu Asp Arg Asp Ser Ile Ser Glu Tyr Ala Cys Gln Arg Arg Thr Thr
            20                  25                  30

Leu Lys Asn Tyr Asn Gln Lys Phe Thr Asp Ala Phe Glu Ile Leu Ala
        35                  40                  45

Glu Asn Tyr Glu Phe Asn Glu Asn Lys Gly Phe Cys Thr Ala Phe Arg
    50                  55                  60

Arg Ala Ala Ser Val Leu Lys Cys Leu Pro Phe Thr Ile Val Gln Val
65                  70                  75                  80

His Asp Ile Glu Gly Val Pro Trp Met Gly Lys Gln Val Lys Gly Ile
                85                  90                  95

Ile Glu Asp Ile Ile Glu Glu Gly Ser Ser Lys Val Lys Ala Val
            100                 105                 110

Leu Asp Asn Glu Asn Tyr Arg Ser Val Lys Leu Phe Thr Ser Val Phe
        115                 120                 125

Gly Val Gly Leu Lys Thr Ser Asp Lys Trp Tyr Arg Met Gly Leu Arg
            130                 135                 140

Thr Leu Glu Glu Val Lys Arg Asp Lys Asn Leu Lys Leu Thr Arg Met
145                 150                 155                 160

Gln Lys Ala Gly Phe Leu His Tyr Asp Leu Thr Ser Cys Val Ser
                165                 170                 175

Lys Ala Glu Ala Asp Ala Ala Ser Leu Ile Val Gln Asp Val Val Trp
            180                 185                 190

Lys Ile Val Pro Asn Ala Ile Val Thr Ile Ala Gly Gly Phe Arg Arg
            195                 200                 205

Gly Lys Gln Thr Gly His Asp Val Asp Phe Leu Ile Thr Val Pro Gly
            210                 215                 220

Ser Lys Gln Glu Glu Glu Leu Leu His Thr Val Ile Asp Ile Trp
225                 230                 235                 240

Lys Lys Gln Glu Leu Leu Leu Tyr Tyr Asp Leu Ile Glu Ser Thr Phe
                245                 250                 255

Glu Asp Thr Lys Leu Pro Ser Arg Lys Val Asp Ala Leu Asp His Phe
            260                 265                 270

Gln Lys Cys Phe Ala Ile Leu Lys Val His Lys Glu Arg Glu Asp Lys
            275                 280                 285

Gly Asn Ser Ile Arg Ser Lys Ala Phe Ser Glu Glu Ile Lys Asp
            290                 295                 300

Trp Lys Ala Ile Arg Val Asp Leu Val Val Val Pro Phe Glu Gln Tyr
305                 310                 315                 320

Ala Phe Ala Leu Leu Gly Trp Thr Gly Ser Thr Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Asn Ala Ala Ser Glu
            355                 360                 365

Glu Glu Ile Phe Ala His Leu Gly Leu Asp Tyr Leu Glu Pro Trp Glu
            370                 375                 380

Arg Asn Ala
385

<210> SEQ ID NO 9
<211> LENGTH: 381
<212> TYPE: PRT
<213> ORGANISM: ARTIFICIAL SEQUENCE
<220> FEATURE:
<223> OTHER INFORMATION: truncated dog

<400> SEQUENCE: 9

Asp Tyr Thr Ala Ser Pro Asn Pro Glu Leu Gln Lys Thr Leu Pro Val
1               5                   10                  15

Ala Val Lys Lys Ile Ser Gln Tyr Ala Cys Gln Arg Arg Thr Thr Leu
            20                  25                  30

Asn Asn Tyr Asn Asn Val Phe Thr Asp Ala Phe Glu Val Leu Ala Glu
                35                  40                  45

Asn Tyr Glu Phe Arg Glu Asn Glu Val Phe Ser Leu Thr Phe Met Arg
            50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Gln Val Lys Cys Ile Ile
                85                  90                  95

-continued

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
    130                 135                 140

Leu Ser Lys Ile Lys Ser Asp Lys Ser Leu Lys Phe Thr Pro Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
    210                 215                 220

Thr Asp Glu Asp Glu Glu Gln Leu Leu Pro Lys Val Ile Asn Leu Trp
225                 230                 235                 240

Glu Arg Lys Gly Leu Leu Leu Tyr Cys Asp Leu Val Glu Ser Thr Phe
                245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His His Gln Arg Val Asp Gly
        275                 280                 285

Gly Lys Cys Ser Gln Gln Glu Gly Lys Thr Trp Lys Ala Ile Arg Val
    290                 295                 300

Asp Leu Val Met Cys Pro Tyr Glu Arg Arg Ala Phe Ala Leu Leu Gly
305                 310                 315                 320

Trp Thr Gly Ser Arg Gln Phe Glu Arg Asp Leu Arg Arg Tyr Ala Ser
                325                 330                 335

His Glu Arg Lys Met Ile Leu Asp Asn His Ala Leu Tyr Asp Lys Thr
            340                 345                 350

Lys Lys Ile Phe Leu Lys Ala Glu Ser Glu Gly Glu Ile Phe Ala His
        355                 360                 365

Leu Gly Leu Asp Tyr Ile Glu Pro Trp Glu Arg Asn Ala
    370                 375                 380

<210> SEQ ID NO 10
<211> LENGTH: 382
<212> TYPE: PRT
<213> ORGANISM: ARTIFICIAL SEQUENCE
<220> FEATURE:
<223> OTHER INFORMATION: TRUNC MOLE

<400> SEQUENCE: 10

Gly Asp Cys Pro Ala Ser His Asp Ser Ser Pro Gln Lys Thr Glu Ser
1               5                   10                  15

Ala Ala Val Gln Lys Ile Ser Gln Tyr Ala Cys Gln Arg Arg Thr Thr
            20                  25                  30

Leu Asn Asn His Asn His Ile Phe Thr Asp Ala Phe Glu Ile Leu Ala
        35                  40                  45

Glu Asn Cys Glu Phe Arg Glu Asn Glu Gly Ser Tyr Val Thr Tyr Met
    50                  55                  60

Arg Ala Ala Ser Val Leu Lys Ser Leu Pro Phe Ser Ile Ile Ser Met
65                  70                  75                  80

Lys Asp Thr Glu Gly Ile Pro Cys Leu Ala Asp Lys Val Lys Cys Val
                85                  90                  95

Ile Glu Glu Ile Ile Glu Asp Gly Glu Ser Ser Glu Val Lys Ala Val
            100                 105                 110

Leu Asn Asp Glu Arg Tyr Lys Ser Phe Lys Leu Phe Thr Ser Val Phe
        115                 120                 125

Gly Val Gly Leu Lys Thr Ala Glu Lys Trp Phe Arg Leu Gly Phe Arg
    130                 135                 140

Thr Leu Ser Gly Ile Met Asn Asp Lys Thr Leu Lys Leu Thr His Met
145                 150                 155                 160

Gln Lys Ala Gly Phe Leu Tyr Tyr Glu Asp Leu Val Ser Cys Val Thr
                165                 170                 175

Arg Ala Glu Ala Glu Ala Val Gly Val Leu Val Lys Glu Ala Val Trp
                180                 185                 190

Ala Phe Leu Pro Asp Ala Ile Val Thr Met Thr Gly Gly Phe Arg Arg
                195                 200                 205

Gly Lys Lys Val Gly His Asp Val Asp Phe Leu Ile Thr Ser Pro Glu
                210                 215                 220

Ala Thr Glu Glu Gln Glu Gln Gln Leu Leu His Lys Val Ile Thr Phe
225                 230                 235                 240

Trp Glu Lys Glu Gly Leu Leu Leu Tyr Cys Asp Leu Tyr Glu Ser Thr
                245                 250                 255

Phe Glu Lys Leu Lys Met Pro Ser Arg Lys Val Asp Ala Leu Asp His
                260                 265                 270

Phe Gln Lys Cys Phe Leu Ile Leu Lys Leu His Arg Glu Cys Val Asp
                275                 280                 285

Asp Gly Thr Ser Ser Gln Leu Gln Gly Lys Thr Trp Lys Ala Ile Arg
                290                 295                 300

Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                325                 330                 335

Thr His Glu Arg Lys Met Met Leu Asp Asn His Ala Leu Tyr Asp Lys
                340                 345                 350

Thr Lys Arg Lys Phe Leu Ser Ala Asp Ser Glu Glu Asp Ile Phe Ala
                355                 360                 365

His Leu Gly Leu Asp Tyr Ile Glu Pro Trp Glu Arg Asn Ala
                370                 375                 380

<210> SEQ ID NO 11
<211> LENGTH: 379
<212> TYPE: PRT
<213> ORGANISM: ARTIFICIAL SEQUENCE
<220> FEATURE:
<223> OTHER INFORMATION: Pika trunk

<400> SEQUENCE: 11

Glu Tyr Ser Ala Asn Pro Ser Pro Gly Pro Gln Ala Thr Pro Ala Val
1               5                   10                  15

Tyr Lys Ile Ser Gln Tyr Ala Cys Gln Arg Arg Thr Thr Leu Asn Asn
                20                  25                  30

His Asn His Ile Phe Thr Asp Ala Phe Glu Ile Leu Ala Glu Asn Tyr
            35                  40                  45

Glu Phe Lys Glu Asn Glu Gly Cys Tyr Val Thr Tyr Met Arg Ala Ala
        50                  55                  60

```
Ser Val Leu Lys Ser Leu Pro Phe Thr Ile Val Ser Met Lys Asp Thr
 65                  70                  75                  80

Glu Gly Ile Pro Cys Leu Glu Asp Lys Val Lys Ser Ile Met Glu Glu
                 85                  90                  95

Ile Ile Glu Glu Gly Glu Ser Ser Glu Val Lys Ala Val Leu Ser Asp
            100                 105                 110

Glu Arg Tyr Gln Cys Phe Lys Leu Phe Thr Ser Val Phe Gly Val Gly
        115                 120                 125

Leu Lys Thr Ser Glu Lys Trp Phe Arg Met Gly Phe Arg Ser Leu Ser
130                 135                 140

Asn Ile Arg Leu Asp Lys Ser Leu Lys Phe Thr Gln Met Gln Lys Ala
145                 150                 155                 160

Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
            180                 185                 190

Pro Asp Ala Phe Ile Thr Met Thr Gly Gly Phe Arg Arg Gly Lys Lys
        195                 200                 205

Ile Gly His Asp Val Asp Phe Leu Ile Thr Ser Pro Glu Leu Thr Glu
210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
                245                 250                 255

Leu Lys Gln Pro Ser Arg Lys Val Asp Ala Leu Asp His Phe Gln Lys
            260                 265                 270

Cys Phe Leu Ile Phe Lys Leu Tyr His Glu Arg Val Gly Gly Asp Arg
        275                 280                 285

Cys Arg Gln Pro Glu Gly Lys Asp Trp Lys Ala Ile Arg Val Asp Leu
290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                325                 330                 335

Arg Lys Met Ile Leu Asp Asn His Ala Leu Tyr Asp Lys Thr Lys Arg
            340                 345                 350

Val Phe Leu Gln Ala Glu Asn Glu Glu Ile Phe Ala His Leu Gly
        355                 360                 365

Leu Asp Tyr Ile Glu Pro Trp Glu Arg Asn Ala
        370                 375

<210> SEQ ID NO 12
<211> LENGTH: 384
<212> TYPE: PRT
<213> ORGANISM: ARTIFICIAL SEQUENCE
<220> FEATURE:
<223> OTHER INFORMATION: TRUNC HEDGEHOG

<400> SEQUENCE: 12

Asp Ala Ser Phe Gly Ser Asn Pro Gly Ser Gln Asn Thr Pro Pro Leu
 1               5                  10                  15

Ala Ile Lys Lys Ile Ser Gln Tyr Ala Cys Gln Arg Arg Thr Ser Leu
                20                  25                  30

Asn Asn Cys Asn His Ile Phe Thr Asp Ala Leu Asp Ile Leu Ala Glu
            35                  40                  45
```

Asn His Glu Phe Arg Glu Asn Glu Val Ser Cys Val Ala Phe Met Arg
            50                  55                  60

Ala Ala Ser Val Leu Lys Ser Leu Pro Phe Thr Ile Ile Ser Met Lys
 65                  70                  75                  80

Asp Thr Lys Gly Ile Pro Cys Leu Gly Asp Lys Ala Lys Cys Val Ile
                     85                  90                  95

Glu Glu Ile Ile Glu Asp Gly Glu Ser Ser Glu Val Lys Ala Ile Leu
                100                 105                 110

Asn Asp Glu Arg Tyr Gln Ser Phe Lys Leu Phe Thr Ser Val Phe Gly
                115                 120                 125

Val Gly Leu Lys Thr Ser Glu Lys Trp Phe Arg Met Gly Phe Arg Thr
130                 135                 140

Leu Asn Lys Ile Met Ser Asp Lys Thr Leu Lys Leu Thr Arg Met Gln
145                 150                 155                 160

Lys Ala Gly Phe Leu Tyr Tyr Glu Asp Leu Val Ser Cys Val Ala Lys
                165                 170                 175

Ala Glu Ala Asp Ala Val Ser Val Leu Val Gln Glu Ala Val Trp Ala
                180                 185                 190

Phe Leu Pro Asp Ala Met Val Thr Met Thr Gly Gly Phe Arg Arg Gly
                195                 200                 205

Lys Lys Leu Gly His Asp Val Asp Phe Leu Ile Thr Ser Pro Gly Ala
210                 215                 220

Thr Glu Glu Glu Glu Gln Gln Leu Leu Pro Lys Val Ile Asn Phe Trp
225                 230                 235                 240

Glu Arg Lys Gly Leu Leu Leu Tyr His Asp Leu Val Glu Ser Thr Phe
                245                 250                 255

Glu Lys Leu Lys Leu Pro Ser Arg Lys Val Asp Ala Leu Asp His Phe
                260                 265                 270

Gln Lys Cys Phe Leu Ile Leu Lys Leu His Leu Gln His Val Asn Gly
                275                 280                 285

Val Gly Asn Ser Lys Thr Gly Gln Gln Glu Gly Lys Asn Trp Lys Ala
290                 295                 300

Ile Arg Val Asp Leu Val Met Cys Pro Tyr Glu Arg Arg Ala Phe Ala
305                 310                 315                 320

Leu Leu Gly Trp Thr Gly Ser Arg Gln Phe Glu Arg Asp Leu Arg Arg
                325                 330                 335

Phe Ala Thr His Glu Arg Lys Met Met Leu Asp Asn His Ala Leu Tyr
                340                 345                 350

Asp Lys Thr Lys Arg Ile Phe Leu Lys Ala Glu Ser Glu Glu Ile
                355                 360                 365

Phe Ala His Leu Gly Leu Asp Tyr Ile Asp Pro Trp Glu Arg Asn Ala
370                 375                 380

<210> SEQ ID NO 13
<211> LENGTH: 381
<212> TYPE: PRT
<213> ORGANISM: ARTIFICIAL SEQUENCE
<220> FEATURE:
<223> OTHER INFORMATION: truncated tree shrew

<400> SEQUENCE: 13

Asp His Ser Thr Ser Pro Ser Pro Gly Pro Gln Lys Thr Pro Ala Leu
 1               5                  10                  15

Ala Val Gln Lys Ile Ser Gln Tyr Ala Cys Gln Arg Arg Thr Thr Leu
                20                  25                  30

Asn Asn Cys Asn Arg Val Phe Thr Asp Ala Phe Glu Thr Leu Ala Glu
            35                  40                  45

Asn Tyr Glu Phe Arg Glu Asn Glu Asp Ser Ser Val Ile Phe Leu Arg
    50                  55                  60

Ala Ala Ser Val Leu Arg Ser Leu Pro Phe Thr Ile Thr Ser Met Arg
65                  70                  75                  80

Asp Thr Glu Gly Leu Pro Cys Leu Gly Asp Lys Val Lys Cys Val Ile
                85                  90                  95

Glu Glu Ile Ile Glu Asp Gly Glu Ser Ser Glu Val Asn Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Leu Val Thr Ile Thr Gly Gly Phe Arg Arg Gly
        195                 200                 205

Lys Lys Thr Gly His Asp Val Asp Phe Leu Ile Thr Ser Pro Gly Ser
    210                 215                 220

Thr Glu Glu Lys Glu Glu Leu Leu Gln Lys Val Leu Asn Leu Trp
225                 230                 235                 240

Glu Lys Lys Gly Leu Leu Leu Tyr Tyr Asp Leu Val Glu Ser Thr Phe
                245                 250                 255

Glu Lys Leu Lys Thr Pro Ser Arg Lys Val Asp Ala Leu Asp His Phe
            260                 265                 270

Pro Lys Cys Phe Leu Ile Leu Lys Leu His His Gln Arg Val Asp Gly
        275                 280                 285

Asp Lys Pro Ser Gln Gln Glu Gly Lys Ser Trp Lys Ala Ile Arg Val
    290                 295                 300

Asp Leu Val Met Cys Pro Tyr Glu Arg His Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Val Phe Leu Lys Ala Glu Ser Glu Glu Asp Ile Phe Ala His
        355                 360                 365

Leu Gly Leu Asp Tyr Ile Glu Pro Trp Glu Arg Asn Ala
    370                 375                 380

<210> SEQ ID NO 14
<211> LENGTH: 394
<212> TYPE: PRT
<213> ORGANISM: ARTIFICIAL SEQUENCE
<220> FEATURE:
<223> OTHER INFORMATION: TRUNCATED PLATYPUS

<400> SEQUENCE: 14

Leu Thr Asn Ser Ala Pro Ile Asn Cys Met Thr Glu Thr Pro Ser Leu
1               5                   10                  15

Ala Thr Lys Gln Val Ser Gln Tyr Ala Cys Glu Arg Arg Thr Thr Leu
            20                  25                  30

Asn Asn Cys Asn Gln Lys Phe Thr Asp Ala Phe Glu Ile Leu Ala Lys
        35                  40                  45

Asp Phe Glu Phe Arg Glu Asn Glu Gly Ile Cys Leu Ala Phe Met Arg
50                  55                  60

Ala Ile Ser Val Leu Lys Cys Leu Pro Phe Thr Ile Val Arg Met Lys
65                  70                  75                  80

Asp Ile Glu Gly Val Pro Trp Leu Gly Asp Gln Val Lys Ser Ile Ile
                85                  90                  95

Glu Glu Ile Ile Glu Asp Gly Ser Ser Val Lys Ala Val Leu
            100                 105                 110

Asn Asp Glu Arg Tyr Arg Ser Phe Gln Leu Phe Asn Ser Val Phe Glu
        115                 120                 125

Val Gly Leu Thr Asp Asn Gly Glu Asn Gly Ile Ala Arg Gly Phe Gln
130                 135                 140

Thr Leu Asn Glu Val Ile Thr Asp Glu Asn Ile Ser Leu Thr Lys Thr
145                 150                 155                 160

Thr Leu Ser Thr Ser Leu Trp Asn Tyr Leu Pro Gly Phe Leu Tyr Tyr
                165                 170                 175

Glu Asp Leu Val Ser Cys Val Ala Lys Glu Glu Ala Asp Ala Val Tyr
            180                 185                 190

Leu Ile Val Lys Glu Ala Val Arg Ala Phe Leu Pro Glu Ala Leu Val
        195                 200                 205

Thr Leu Thr Gly Gly Phe Arg Arg Gly Lys Lys Ile Gly His Asp Val
210                 215                 220

Asp Phe Leu Ile Ser Asp Pro Glu Ser Gly Gln Asp Glu Gln Leu Leu
225                 230                 235                 240

Pro Asn Ile Ile Lys Leu Trp Glu Lys Gln Glu Leu Leu Tyr Tyr
                245                 250                 255

Asp Leu Val Glu Ser Thr Phe Glu Lys Thr Lys Ile Pro Ser Arg Lys
            260                 265                 270

Val Asp Ala Met Asp His Phe Gln Lys Cys Phe Leu Ile Leu Lys Leu
        275                 280                 285

His His Gln Lys Val Asp Ser Gly Arg Tyr Lys Pro Pro Glu Ser
290                 295                 300

Lys Asn His Glu Ala Lys Asn Trp Lys Ala Ile Arg Val Asp Leu Val
305                 310                 315                 320

Met Cys Pro Phe Glu Gln Tyr Ala Tyr Ala Leu Leu Gly Trp Thr Gly
                325                 330                 335

Ser Arg Gln Phe Glu Arg Asp Leu Arg Arg Tyr Ala Thr His Glu Lys
            340                 345                 350

Lys Met Met Leu Asp Asn His Ala Leu Tyr Asp Lys Thr Lys Lys Ile
        355                 360                 365

Phe Leu Lys Ala Glu Ser Glu Glu Asp Ile Phe Thr His Leu Gly Leu
370                 375                 380

Asp Tyr Ile Glu Pro Trp Glu Arg Asn Ala
385                 390

<210> SEQ ID NO 15
<211> LENGTH: 384
<212> TYPE: PRT
<213> ORGANISM: ARTIFICIAL SEQUENCE
<220> FEATURE:

<223> OTHER INFORMATION: TRUNCATED JERBOA

<400> SEQUENCE: 15

```
Ser Ser Glu Leu Glu Leu Leu Asp Val Ser Trp Leu Ile Glu Cys Met
1               5                   10                  15

Gly Ala Gly Lys Pro Val Glu Met Thr Gly Arg His Gln Leu Val Lys
            20                  25                  30

Gln Thr Phe Cys Leu Pro Gly Phe Ile Leu Gln Asp Ala Phe Asp Ile
        35                  40                  45

Leu Ala Glu Asn Cys Glu Phe Arg Glu Asn Glu Ala Ser Cys Val Glu
    50                  55                  60

Phe Met Arg Ala Ala Ser Val Leu Lys Ser Leu Pro Phe Pro Ile Ile
65                  70                  75                  80

Ser Val Lys Asp Thr Glu Gly Ile Pro Trp Leu Gly Gly Lys Val Lys
                85                  90                  95

Cys Val Ile Glu Glu Ile Ile Glu Asp Gly Glu Ser Ser Glu Val Lys
            100                 105                 110

Ala Leu Leu Asn Asp Glu Arg Tyr Lys Ser Phe Lys Leu Phe Thr Ser
        115                 120                 125

Val Phe Gly Val Gly Leu Lys Thr Ala Glu Arg Trp Phe Arg Met Gly
    130                 135                 140

Phe Arg Thr Leu Ser Thr Val Lys Leu Asp Lys Ser Leu Thr Phe Thr
145                 150                 155                 160

Arg Met Gln Lys Ala Gly Phe Leu His Tyr Glu Asp Leu Val Ser Cys
                165                 170                 175

Val Thr Arg Ala Glu Ala Glu Ala Val Ser Val Leu Val Gln Gln Ala
            180                 185                 190

Val Val Ala Phe Leu Pro Asp Ala Leu Val Ser Met Thr Gly Gly Phe
        195                 200                 205

Arg Arg Gly Lys Lys Ile Gly His Asp Val Asp Phe Leu Ile Thr Ser
    210                 215                 220

Pro Glu Ala Thr Glu Glu Glu Gln Gln Leu Leu His Lys Val Thr
225                 230                 235                 240

Asn Phe Trp Glu Gln Lys Gly Leu Leu Leu Tyr Cys Asp His Val Glu
                245                 250                 255

Ser Thr Phe Glu Lys Cys Lys Leu Pro Ser Arg Lys Val Asp Ala Leu
            260                 265                 270

Asp His Phe Gln Lys Cys Phe Leu Ile Leu Lys Leu Tyr Arg Glu Arg
        275                 280                 285

Val Asp Ser Val Lys Ser Ser Gln Gln Glu Gly Lys Gly Trp Lys Ala
    290                 295                 300

Ile Arg Val Asp Leu Val Met Cys Pro Tyr Glu Cys Arg Ala Phe Ala
305                 310                 315                 320

Leu Leu Gly Trp Thr Gly Ser Arg Gln Phe Glu Arg Asp Leu Arg Arg
                325                 330                 335

Tyr Ala Thr His Glu Arg Lys Met Arg Leu Asp Asn His Ala Leu Tyr
            340                 345                 350

Asp Lys Thr Lys Arg Val Phe Leu Lys Ala Glu Ser Glu Glu Glu Ile
        355                 360                 365

Phe Ala His Leu Gly Leu Glu Tyr Ile Glu Pro Leu Glu Arg Asn Ala
    370                 375                 380
```